United States Patent [19]

Cecchi et al.

[11] Patent Number: 5,130,339

[45] Date of Patent: Jul. 14, 1992

[54] PHENYLETHANOLAMINOMETHYLTETRALINS AND PHARMACEUTICAL USE

[75] Inventors: Roberto Cecchi, Lodi; Umberto Guzzi, Milan, both of Italy

[73] Assignee: Sanofi, Paris, France

[21] Appl. No.: 301,050

[22] Filed: Dec. 28, 1990

[30] Foreign Application Priority Data

Dec. 29, 1989 [FR] France .................. 89 17465
Nov. 26, 1990 [EP] European Pat. Off. ...... 90/403342.0

[51] Int. Cl.$^5$ ............................................. A61K 31/135
[52] U.S. Cl. ............................ 514/653; 514/510; 514/561; 514/564; 514/650; 560/20; 560/42; 562/451; 564/337; 564/338; 564/363; 564/365
[58] Field of Search ............... 564/363, 337, 338, 365; 514/653, 510, 561, 564, 650; 560/20, 42; 562/451

[56] References Cited

U.S. PATENT DOCUMENTS 4,707,497  11/1987  Cecchi et al. ............ 514/647
4,833,169   5/1989  von Sprecher et al. ..... 514/530
4,939,160   7/1990  von Sprecher et al. ..... 514/318

FOREIGN PATENT DOCUMENTS 0211721  2/1987  European Pat. Off. .
0213080  3/1987  European Pat. Off. .
0303545  2/1989  European Pat. Off. .
0325963  8/1989  .

OTHER PUBLICATIONS

Schaaf et al., *Journal of Medicinal Chemistry*, vol. 26, No. 3, pp. 328–334, 1983.

Primary Examiner—Richard L. Raymond
Assistant Examiner—Scott C. Rand
Attorney, Agent, or Firm—Bacon & Thomas

[57] ABSTRACT

New phenylethanolaminomethyltetralins of formula (I)

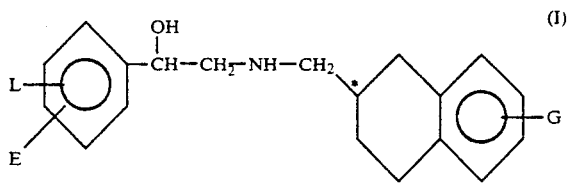

wherein
  E represents hydrogen, $(C_1-C_4)$alkyl, $(C_1-C_4)$alkoxy, phenyl, nitro, halogen, or trifluoromethyl,
  L represents hydrogen, $(C_1-C_4)$alkyl, $(C_1-C_4)$alkyoxy, phenyl, nitro, or halogen, or
  E and L taken together represent a group —CH=CH—CH=CH— or —CH$_2$—CH$_2$—CH$_2$—CH$_2$—, and
  G represents hydrogen, chloro, hydroxy or an —OG' group wherein G' represents a $(C_1-C_4$(alkyl group either unsubstituted or substituted with hydroxy, $(C_1-C_4)$alkoxy, $(C_1-C_4)$alkoxycarbonyl, carboxy, or $(C_3-C_7)$cycloalkyl; a $(C_3-C_7)$cycloalkyl group; or a $(C_2-C_4)$alkanoyl group; and salts thereof, are described which showed to be active as intestinal motility modulating agents and intraocular hypertension lowering agents.

Also described is a process for the preparation of the new compounds and the intermediates of formula (III)

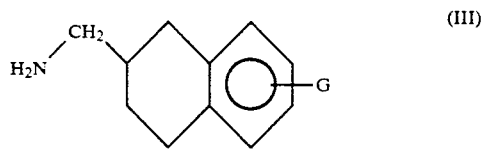

employed in said process.

7 Claims, No Drawings

PHENYLETHANOLAMINOMETHYLTETRALINS AND PHARMACEUTICAL USE

The present invention relates to new phenylethanolaminomethyltetralins, a process for the preparation thereof, the intermediates in said process and the pharmaceutical compositions containing said phenylethanolaminomethyltetralins as the active principles.

European Patent 211,721 describes phenylethanolaminotetralins substituted on the aromatic ring of the tetralin moiety of following formula (A):

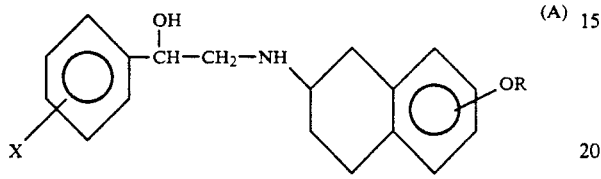

wherein X represents hydrogen, halogen, trifluoromethyl, or lower alkyl and R represents hydrogen, unsubstituted methyl or methyl substituted with carboxy or alkoxycarbonyl, endowed with very interesting pharmacological properties. Compounds (A) are indicated inter alia as intestinal and uterine motility modulators.

It has now been found that compounds which differ from the compounds known essentially in the presence of a methylene group (—CH$_2$—) between the tetralin moiety and the amino group, have an intestinal motility modulating activity higher than or at least equal to the activity of the corresponding known phenylethanolaminotetralins, associated with a higher selectivity towards the intestine.

In one of its embodiments, therefore the present invention concerns phenylethanolaminomethyltetralins of following formula (I) :

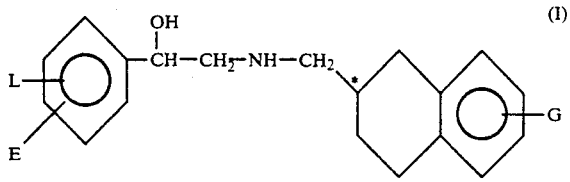

wherein
E represents hydrogen, (C$_1$-C$_4$)alkyl, (C$_1$-C$_4$)alkoxy, phenyl, nitro, halogen, or trifluoromethyl,
L represents hydrogen, (C$_1$-C$_4$)alkyl, (C$_1$-C$_4$)alkoxy, phenyl, nitro, or halogen, or
E and L taken together represent a group —CH=CH—CH=CH— or —CH$_2$—CH$_2$—CH$_2$—CH$_2$—, and
G represents hydrogen, chloro, hydroxy or an —OG' group wherein G' represents a (C$_1$-C$_4$)alkyl group either unsubstituted or substituted with hydroxy, (C$_1$-C$_4$)alkoxy, (C$_1$-C$_4$)alkoxycarbonyl, carboxy, or (C$_3$-C$_7$)cycloalkyl; a (C$_3$-C$_7$)cycloalkyl group; or a (C$_2$-C$_4$)alkanoyl group; and their salts.

As used herein
the term "(C$_1$-C$_4$)alkyl" designates a monovalent radical of a saturated, straight or branched hydrocarbon which may contain from 1 to 4 carbon atoms, such as methyl, ethyl, propyl, isopropyl, n-butyl, sec-butyl or tert-butyl;
the term "(C$_1$-C$_4$)alkoxy" designates a straight or branched alkoxy radical of from 1 to 4 carbon atoms, such as methoxy, ethoxy, propoxy, isopropoxy, n-butoxy, sec-butoxy, or tert-butoxy;
the term "(C$_3$-C$_7$)cycloalkyl" identifies a monovalent radical of a saturated cyclic hydrocarbon of from 3 to 7 carbon atoms, such as cyclopropyl, cyclobutyl, cyclopentyl, cyclopentyl substituted with one or two methyl groups or with an ethyl group, or cyclohexyl, methyl-cyclohexyl, or cycloheptyl;
the term "(C$_2$-C$_4$)alkanoyl" designates an acyl radical deriving from an aliphatic saturated carboxylic acid containing from 2 to 4 carbon atoms, i.e. acetyl, propionyl, 2-methylpropionyl, and butyryl;
the term "halogen" includes the four forms thereof fluoro, chloro, bromo, and iodo, the former three being preferred;
the terms "tetralin" and "tetralone" actually refers to the 1,2,3,4-tetrahydronaphthalene ring.

The term "salts" of the compounds of formula (I) according to the present invention, includes the addition salts with pharmaceutically acceptable mineral or organic acids such as the hydrochloride, hydrobromide, sulfate, hydrogensulfate, dihydrogenphosphate, citrate, maleate, tartrate, fumarate, gluconate, methanesulfonate, 2-naphthalenesulfonate, and the like, as well as the addition salts which allow an easy separation or crystallisation of the compounds of formula (I), such as the picrate and the oxalate, or the addition salts with optically active acids, such as camphorsulfonic acids, mandelic or substituted mandelic acids.

Moreover, when the compounds of formula (I) contain a free carboxy group, the term "salts" also includes the salts thereof with mineral bases, preferably those with alkali metals such as sodium or potassium, or with organic bases, such as trometamol.

In the above formula (I), the two asymmetric carbons are marked by an asterisk. All the compounds of formula (I) may therefore exist as four different stereoisomers (R,R), (R,S), (S,R), and (S,S). The optically pure isomers, as well as the mixtures of two, three or all the four isomers, in any proportion, are part of the present invention. Other asymmetric centres might be present in the E, L and G groups. Analogously, the stereoisomers deriving from the presence of said additional chiral centres and their mixtures are part of the present invention.

For the expression of the pharmacological activity, the preferred configuration of the chiral carbon of the ethanolamino moiety is anyway the (R) absolute configuration. The class of compounds of formula (I) wherein E, L, and G are as defined above and the chiral carbon of the ethanolamino chain has the (R) absolute configuration represents therefore a preferred embodiment of the invention.

A preferred group of compounds of the present invention comprises those compounds of formula (I) wherein E and L are as defined above and G represents hydrogen, hydroxy or an —OG' group wherein G' represents (C$_1$-C$_4$)alkyl either unsubstituted or substituted with hydroxy, (C$_1$-C$_4$)alkoxy, carboxy, (C$_1$-C$_4$)alkoxycarbonyl, or (C$_3$-C$_7$)cycloalkyl, and their salts.

Particularly preferred compounds of the present invention are those compounds of formula (I) wherein E is hydrogen, (C$_1$-C$_4$)alkyl or halogen, L is hydrogen and G represents hydrogen, hydroxy or an —OG' group wherein G' represents unsubstituted $(C_1-C_4)$alkyl or $(C_1-C_4)$alkyl substituted with carboxy or $(C_1-C_4)$ alkoxycarbonyl, and their salts.

The compounds of formula (I) may be prepared by treating a compound of formula (II)

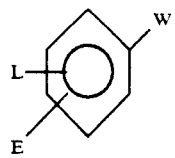
(II)

wherein E and L are as defined above and the radical —W represents one of the following groups:

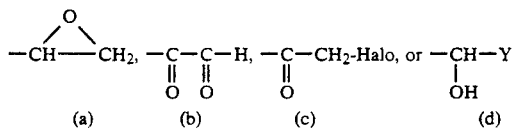

wherein Halo stands for chloro, bromo, or iodo, and Y is a —COOH group or a functional derivative thereof; with a compound of formula (III)

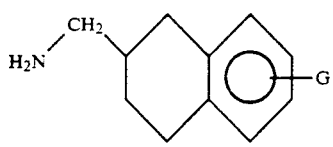
(III)

wherein G is as defined above, and, when —W is different from

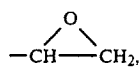

treating the thus obtained product with a suitably selected reducing agent.

More particularly, the reaction between the compounds of formula (II) and the 2-aminomethyltetralin derivative of formula (III) is carried out under different reaction conditions which essentially depend on the nature of the starting compound of formula (II) and mainly on the meaning of —W.

Said operative techniques, which are described in details hereinbelow, have been designated as Methods (a) to (d).

Method (a)

According to said method, opening of the epoxide of formula (IIa)

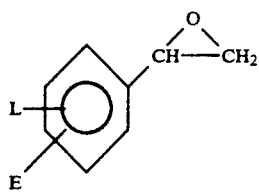
(IIa)

by the amine of formula (III) is carried out in an organic solvent such as a lower alkanol, e.g. methanol, ethanol, and isopropanol, a cyclic or linear ether, or an amide such as dimethylformamide or dimethylacetamide, using an at least equimolar amount of the two reactants but preferably an excess of the amine of formula (III). The reaction temperature is typically comprised between room temperature and the reflux temperature of the selected solvent. A basic agent, such as triethylamine, sodium hydroxide or sodium acetate, may conveniently be employed.

Method (b)

In the reaction which involves condensation of the phenylglyoxal of formula (IIb)

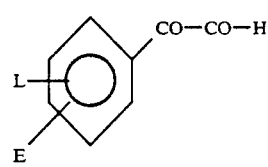
(IIb)

with the amine of formula (III) and reduction of the obtained product, the preferred operating conditions involve carrying out the two reactions simultaneously, by contacting the compound of formula (IIb) with that of formula (III) in the presence of a suitably selected reducing agent. If the amine of formula (III) and the phenylglyoxal of formula (IIb) do not contain groups which are susceptible to reduction conditions, the reaction may be carried out by catalytic hydrogenation in the presence, for instance, of platinum dioxide or Raney nickel, and of an alcoholic solvent, such as methanol or ethanol, at the atmospheric pressure or under pressure. According to alternative operating conditions, an alkali metal hydride such as sodium borohydride, may be used, in the presence of an alcoholic solvent, such as ethanol, preferably at low temperatures.

Method (c)

According to another method, the compounds of formula (I) are prepared by reacting the amine of formula (III) with an α-halo-acetophenone of formula (IIc)

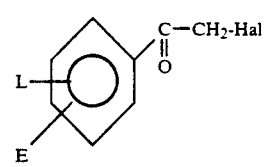
(IIc)

in an inert solvent, such as a linear or cyclic ether, a lower alkanol, such as methanol, ethanol, or isopropanol, an aromatic hydrocarbon such as toluene, or benzene, a halogenated aliphatic hydrocarbon such as chloroform, or a nitrile, such as acetonitrile.

This nucleophilic substitution is advantageously carried out at room temperature of in the cold. Reduction of the thus obtained product may be achieved according to known techniques such as for instance by catalytic hydrogenation in the presence of e.g. palladium on carbon, Raney nickel, or platinum dioxide, in an alcoholic solvent, such as methanol or ethanol, preferably at low temperatures; or by the addition of lithium aluminum hydride in ethyl ether or in tetrahydrofuran, or, by the action of an aluminum alkoxide, such as aluminum isopropoxide, in a solvent such as isopropanol, preferably at the reflux temperature, or also by the action of NaCNBH₃ at a pH of about 5.

Method (d)

According to an alternative operating method, which represents a preferred embodiment of the present invention, the amine of formula (III) is reacted with a compound of formula (IId)

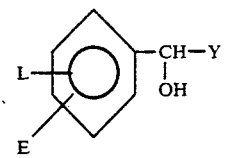

wherein E, L, and Y are as defined above.

As carboxy functional derivatives, there may be employed acyl chlorides, anhydrides, mixed anhydrides, active esters or suitably activated free acids, for instance by means of dicyclohexylcarbodiimide (DCCI) or benzotriazolyl-N-oxytris-(dimethylamino)phosphonium hexafluorophosphate (BOP). The reaction between the compound of formula (IId) above and the aminomethyl-tetralin (III) is carried out in an aprotic, non-polar or, preferably, polar, organic solvent, such as dimethylformamide, dimethylsulfoxide, methylene chloride, benzene, and toluene, optionally in the presence of a proton acceptor, such as an aliphatic tertiary amine, e.g. triethylamine.

The thus obtained mandelamide of formula (IV)

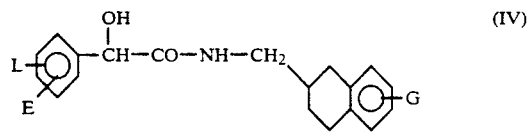

may be submitted directly to reduction of the amido group to methyleneamino.

The reduction step is carried out, for instance, by the action of a hydride, such as lithium aluminum hydride, or of a diborane, particularly of a reactant generating the diborane such as the complex between borane and dimethylsulfide, hereinafter designated as "borane-methyl sulfide". The reaction is carried out in an organic solvent such as tetrahydrofuran, and the thus obtained compound of formula (I) is isolated according to conventional techniques. When a mandelamide of formula (IV) is reduced wherein G is an —OG' group, wherein G' represents alkyl substituted with an optionally salified carboxy group or with a (C₁-C₄)alkoxycarbonyl group, selective reduction of the amido group may be achieved by using borane-methyl sulfide and carrying out the reaction at low temperatures (10°-25° C.).

When the desired product of formula (I) contains one or more groups which are susceptible to reduction conditions, it is generally preferred to use, as the starting material (II), a compound of formula (IIa) or to suitably select, among those known in the literature, particular reducing agents and/or conditions which selectively or at least preferably, afford reduction of the chain between the amino group and the benzene cycle, with formation of the desired —CH(OH)—CH₂—NH— chain without altering the other groups.

Another general method for the preparation of the compounds of formula (I) wherein G is an —OG' group, involves conversion of the compounds (I) wherein G is a hydroxy group, prepared by any of the above methods, into the desired products by conventional O-alkylation or O-acylation by reaction of a compound of formula (I) wherein G is a hydroxy group with an alkylating or acylating agent of formula D—G' wherein G' is as defined above and D represents a good leaving group.

This method is mostly preferred when G is an —OG' group wherein G' represents (C₁-C₄)alkyl substituted with carboxy or (C₁-C₄)alkoxycarbonyl, or (C₂-C₄)alcanoyl.

For example, O-alkylation may be carried out with optionally substituted (C₁-C₄)alkyl halides, i.e. chlorides, iodides, or, preferably, bromides, in the presence of a basic condensation agent.

The O-alkylation reaction is carried out in polar, aprotic, organic solvents such as acetone, esters such as ethyl acetate, or ethers, preferably a cyclic ether such as tetrahydrofuran or dioxane.

As basic condensation agents, there may be employed alkali or alkaline-earth metal carbonates such as sodium, potassium, or calcium carbonates, or tertiary aliphatic amines, such as triethylamine.

O-acylation with (C₂-C₄)alkanoyl halides may be carried out in an aqueous or non-aqueous reaction medium, for instance aqueous ketones such as aqueous acetone, esters such as ethyl acetate, halogenated hydrocarbons such as methylene chloride, amides such as dimethylformamide, nitriles such as acetonitrile or mixtures of two or more of the above solvents.

The reaction temperature is comprised between —50° and +50° C., typically between —20° and +30° C., and preferably the reaction is carried out in the presence of a proton acceptor which blocks the hydrohalic acid which forms during the reaction.

As proton acceptor agents, there may be cited the tertiary amines, such as for instance triethylamine, dimethylaniline, or 4-dimethylaminopyridine, and the inorganic bases such as sodium, potassium or calcium carbonates.

The acylation may also be carried out using a carboxylic acid as the acylating agent. In this case the reaction is advantageously carried out in the presence of a condensation agent such as a carbodiimide, e.g. DCCI, a carbonyl compound, e.g. carbonyldiimidazole, or an isoxazolium salt, e.g. N-ethyl-5-phenyl-isoxazolium perchlorate. O-acylation may also be carried out with other functional derivatives such as for instance activated esters, symmetrical anhydrides or mixed anhydrides. The acylation reactions involving the free acids or their above mentioned functional derivatives are advantageously carried out in an anhydrous reaction medium, for instance in methylene chloride, tetrahydrofuran, dimethylformamide, or acetonitrile. In some particular cases, alternative methods for introducing the G' groups can be easily envisaged, said methods being well known in conventional chemistry.

The compounds of formula (I) wherein G' is an alkyl group substituted with carboxy may be easily prepared for instance through saponification of the corresponding esters.

The compounds of formula (I) wherein G is an —OG' group, wherein G' is 1-methyl-1-(C₁-C₄)alkoxycarbonyl-ethyl or 1-ethyl-1-(C₁-C₄)alkoxycarbonyl-ethyl, may be prepared by reaction of the corresponding compounds (I) wherein G is hydroxy with a compound of formula

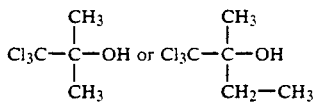

respectively, in the presence of a base, followed by reaction with thionyl chloride in the ($C_1$-$C_4$)alkanol corresponding to the desired ester (J.Am.Chem.Soc., 1948, 70, 1153).

The O-alkylation and O-acylation reactions may be carried out directly on the compounds of formula (I) with a hydroxy group in the tetralin aromatic ring, but in order to avoid N-alkylation or N-acylation side-reactions, the amino group is preferably protected with a temporary protecting group R' before submitting the compounds (I) to said reactions. Suitable protecting groups R' are all the conventional groups which may be removed by catalytic hydrogenation or mild acid hydrolysis, such as benzyloxycarbonyl, substituted benzyloxycarbonyl such as methoxy- or nitro-benzyloxycarbonyl, t-alkoxycarbonyl, such as tert-butoxycarbonyl (Boc), or tert-amyloxycarbonyl (Aoc); the Boc group being particularly preferred.

Introduction of the N-protecting R' group, is achieved by reacting the compounds of formula (I) wherein G is hydroxy with the reactants suitable for the protection of the amino groups as described for instance by M. Bodanszky et al., in Peptide Synthesis, $2^{nd}$ Edition, John Wiley & Sons, 1976, pages 18 and 49, Chapters 3 to 6.

The Boc and Aoc groups for instance may be introduced by reacting di-tert-butyl- and di-tert-amyl-dicarbonates respectively under basic conditions and in the presence of an organic solvent such as dioxane, tetrahydrofuran, or dimethylformamide.

The benzyloxycarbonyl and substituted benzyloxycarbonyl groups may be introduced by the general procedure described by E. C. Horning, in Organic Synthesis, Vol. III, Wiley, New York, 1955, page 167.

The thus obtained compounds of formula (I')

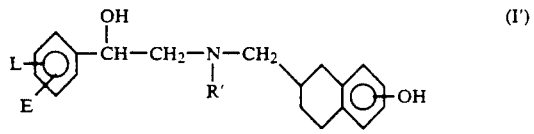

wherein E, L and R' are as defined above are then submitted to O-alkylation or O-acylation according to the general, conventional, methods described above and then the protecting group R' of the thus obtained compounds of formula (I'')

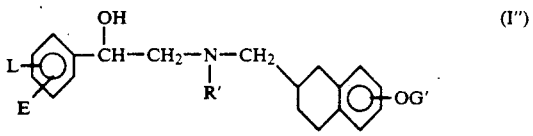

wherein E, L, R', and G' are as defined above, is removed. Removal of the N-protecting groups is achieved by catalytic hydrogenation or mild acidic hydrolysis according to well known literature methods.

Particularly, the Boc and Aoc groups are removed under acidic conditions, by the action of trifluoroacetic acid. The benzyloxycarbonyl and substituted benzyloxycarbonyl groups are cleaved off by catalytic hydrogenation preferably using palladium on carbon as the catalyst.

When a compound of formula (I'') is obtained wherein G' represents an alkyl group substituted with ($C_1$-$C_4$)alkoxycarbonyl, it may be saponified under basic conditions either before or after deprotection of the amino group.

The compounds of formula (I) are isolated according to conventional methods, preferably as the corresponding addition salts with mineral or organic acids which suitably allow separation or crystallisation thereof as indicated above, such as picric acid, oxalic acid, or the optically active acids such as mandelic or substituted mandelic acids, or camphorsulfonic acids, or with the mineral or organic acids which form pharmaceutically acceptable salts such as hydrochloric acid, hydrobromic acid, sulfuric acid, phosphoric acid, methanesulfonic acid, methylsulfuric acid, maleic acid, fumaric acid, and naphthalensulfonic acid.

the free base may be restored by neutralisation and converted into another of its acid addition salts or, when G is an —OG' group wherein G' represents an alkyl group substituted with carboxy, it may be converted into one of its metal salts, typically one of its alkali or alkaline-earth metal salts, such as the sodium or calcium salts.

The compounds of formula (I) which contain only those two asymmetric carbon atoms which are marked by the asterisks may exist as four different stereoisomers.

The process of the present invention may be carried out either on racemates or optically pure isomers. In particular, the reactions involved in the above processes do not modify the stereochemistry of the compounds concerned.

Thus, starting from a compound of formula (IIb) or (IIc), which do not contain any chiral carbon, or a compound of formula (IId) or (IIa) as the racemate and a compound of formula (III) as the racemate, a mixture of the four possible isomers is obtained, i.e. a mixture of the (R,R), (R,S), (S,R), and (S,S) isomers.

Analogously, starting from a compound of formula (III) in optically pure form, a mixture of only two isomers is obtained (e.g. starting from a compound of formula (III) with the (R) absolute configuration, a mixture of the (R,R) and (S,R) isomers is obtained). If also the compound of formula (IIa) or (IId) is employed in optically pure form, the pure isomers (I) are easily obtained.

When a mixture of four isomers is obtained, it may be resolved into the two couples of enantiomers, which are diastereoisomers of each other, i.e. (R,R)+(S,S) and (R,S)+(S,R), by means of known techniques such as fractional crystallisation from a suitable solvent, preferably a lower alkanol, such as ethanol, isopropanol and their mixtures. Each couple of two enantiomers may then be separated into the pure isomers typically by formation of diastereoisomeric salts, or by chromatography on chiral columns, or by any other suitable technique.

When one of the starting compounds is in optically pure form, the thus obtained mixture of two diastereoisomers is separated into the two pure isomers by the above cited methods.

The starting compounds of formula (II) are known products, or they can be easily prepared by conventional methods described in the chemical literature. As an example, the compounds of formula (IIa) may be prepared by epoxidation of the corresponding styrene derivatives with oxygen in the presence of silver-based catalysts, or by the action of dimethylsulfonium or dimethylsulfoxonium methylide on the corresponding substituted benzaldehyde according to the method described by E. J. Corey in J.Am.Chem.Soc., 1956, 87, 1353.

According to a preferred method of preparation, a compound of formula (IIa) in optically pure form can be obtained by reduction of the corresponding substituted mandelic acid having the suitably selected absolute configuration at the chiral carbon, into the corresponding glycol, esterification of the primary alcohol group with a functional derivative of a sulfonic acid, such as tosyl chloride or mesyl chloride, and then cyclisation of the thus obtained compound by treatment with a strong base, such as an alkali metal hydroxide, under the conditions conventionally employed in intramolecular nucleophilic substitutions.

The compounds of formula (IIb) are easily prepared by the action of an oxidizing agent, such as selenium dioxide, on the corresponding acetophenones, in water or in an organic solvent, e.g. a cyclic ether, such as dioxane or tetrahydrofuran.

According to a different method of preparation, said compounds of formula (IIb) are obtained by the action of dimethylsulfoxide on the corresponding haloacetophenones of formula (IIc) by the method described by N. Kornblum in J. Am. Chem. Soc., 1957, 79, 6562, or even starting from the corresponding dihaloacetophenones by the reaction described by F. Venier in C. R. Acad. Sci., 1968, 266, 1650.

The starting compounds of formula (IIc) are easily prepared by halogenation of the corresponding ketones or in some instances by a Friedel-Craft reaction using the corresponding substituted benzene derivatives and a haloacetic acid halide.

Finally, the functional derivatives of mandelic or substituted mandelic acids of formula (IId) are prepared from the corresponding acids which in their turn may be obtained by hydrolysis of mandelonitriles. These last compounds may be prepared starting from either substituted or unsubstituted benzaldehyde and hydrogen cyanide or from either unsubstituted or substituted benzaldehyde, sodium cyanide and sodium bisulfite according to well known literature methods. Mandelic acids of formula (IId) obtained as racemates can be easily separated into the optically pure isomers by forming the diastereoisomeric salts with suitable optically active bases according to well known methods and procedures.

The compounds of formula (III) wherein G represents a chlorine atom, a hydroxy group or an —OG' group wherein G' is as defined above, except the compounds of formula (III) wherein G is a 7- or 8-methoxy group, as well as the optically pure isomers of the compounds of formula (III) wherein G represents hydrogen, chloro, hydroxy or an —OG' group wherein G' has the same meaning as above and their possible salts, are new products and represent the key intermediates in the preparation of the compounds of formula (I). Said compounds of formula (III) represent therefore a further specific object of the present invention.

A preferred group of compounds of formula (III) comprises those compounds of formula (III) wherein G represents hydroxy or an —OG' group wherein G' represents $(C_1-C_4)$alkyl substituted with carboxy or $(C_1-C_4)$alkoxycarbonyl.

The compounds of formula (III) can be prepared starting from a 1-tetralone derivative of formula (V)

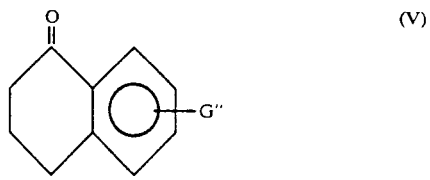

wherein G" represents hydrogen, chloro, hydroxy or methoxy, according to a general method which is outlined in Scheme I below:

Scheme I

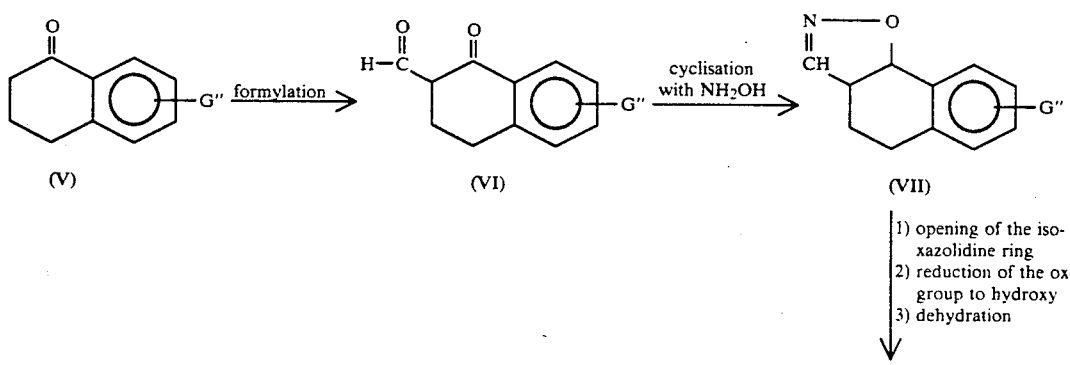

1) opening of the isoxazolidine ring
2) reduction of the oxo group to hydroxy
3) dehydration -continued
Scheme I

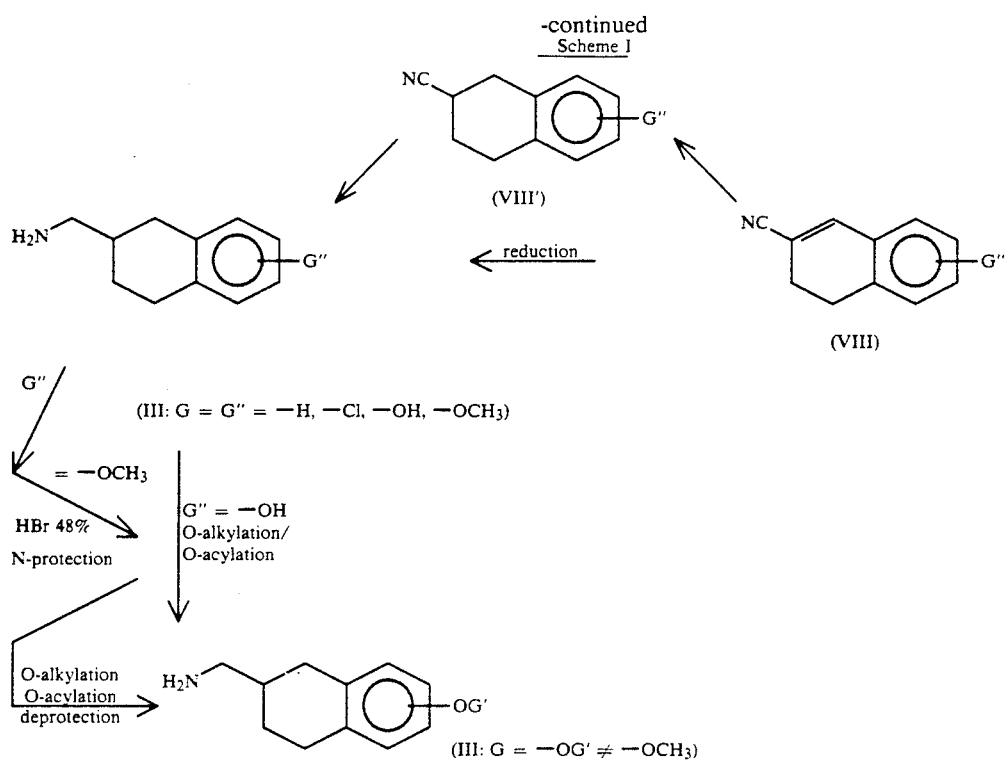

The sequence of reactions illustrated in Scheme I involves (i) a Claisen reaction to introduce a 2-formyl group into the 1-tetralone derivative (V), through reaction with an alkyl formate in the presence of sodium, (ii) reaction of the thus obtained compound of formula (VI) with hydroxylamine under heating in acidic medium, (iii) opening of the isoxazolidine ring of the compound (VII) and reduction of the 1-oxo group to 1-hydroxy (e.g. by the method described in Synthesis, 1981, 449), (iv) dehydration of the obtained intermediate compound with a dehydrating system, e.g. $POCl_3$/pyridine, and (v) treatment of the thus obtained compound of formula (VIII) with a suitable reducing agent to afford the corresponding compound of formula (III) wherein G =G" and represents hydrogen, chloro, hydroxy or methoxy.

Reduction of the compounds of formula (VIII) may be carried out in two steps, e.g. with sodium borohydride first and then with lithium aluminum hydride or isobutylaluminum hydride (DIBAL), or in a single step, e.g. using directly $LiAlH_4$ or DIBAL. In the former case, the 2-cyano-tetralin optionally substituted with a G" group may be isolated.

The compounds of formula (III) wherein G is an —OG' group different from methoxy are then prepared by O-alkylation or O-acylation of the compound (III) wherein G=G"=—OH by the conventional methods described above for the O-alkylation and O-acylation of the compounds of formula (I) wherein G is a hydroxy group. Also in this case, the optional O-alkylation and O-acylation of the compound of formula (III) wherein G=G"=—OH may be carried out preferably with prior protection of the amino group. For prior protection of the amino group there may be employed not only the N-protecting groups R' listed above for protection of the —NH— group of compounds (I) but also 2,2,2-trichloroethyl, benzyl, benzhydryl, and trityl groups either unsubstituted or substituted on the benzene ring or on one of the benzene rings with methoxy or nitro, or it is also possible to form phthalimido derivatives. Removal of said protecting groups is achieved by conventional techniques, typically by catalytic hydrogenation with palladium or palladium hydroxide on carbon when 2,2,2-trichloroethyl or optionally substituted benzyl, benzhydryl, or trityl groups are used and by treatment with hydrazine when phthalimido groups are formed. Trityl and methoxytrityl groups can be removed also by mild hydrolysis, e.g. 50 % HCOOH.

The compounds of formula (III) wherein G is a hydroxy group may also be prepared starting from a compound of formula (V) wherein G" is a methoxy group at the same position and submitting the compounds of formula (III) obtained by the general method described in Scheme I to a demethylation reaction with hydrobromic acid.

Also, the compounds of formula (III) wherein G is an —OG' group, wherein G' is ethyl substituted with carboxy or ($C_1$-$C_4$)alkoxycarbonyl, may be prepared starting from the corresponding compounds (III) wherein G is an —OG' group, wherein G' is methyl substituted with carboxy by protection of the amino group with a Boc or Aoc group, followed by the Arndt-Eistert reaction (Ber., 1935, 68, 200) which involves conversion of the acid into the corresponding acyl chloride followed by reaction of this last product with diazomethane and hydrolysis in the presence of $Ag_2O$.

The 2-cyano-3,4-dihydronaphthalene derivatives of formula (VIII) may also be prepared starting from the corresponding 2-tetralones of formula (IX)

1-tetralones (V) by a general method which is outlined in Scheme II below:

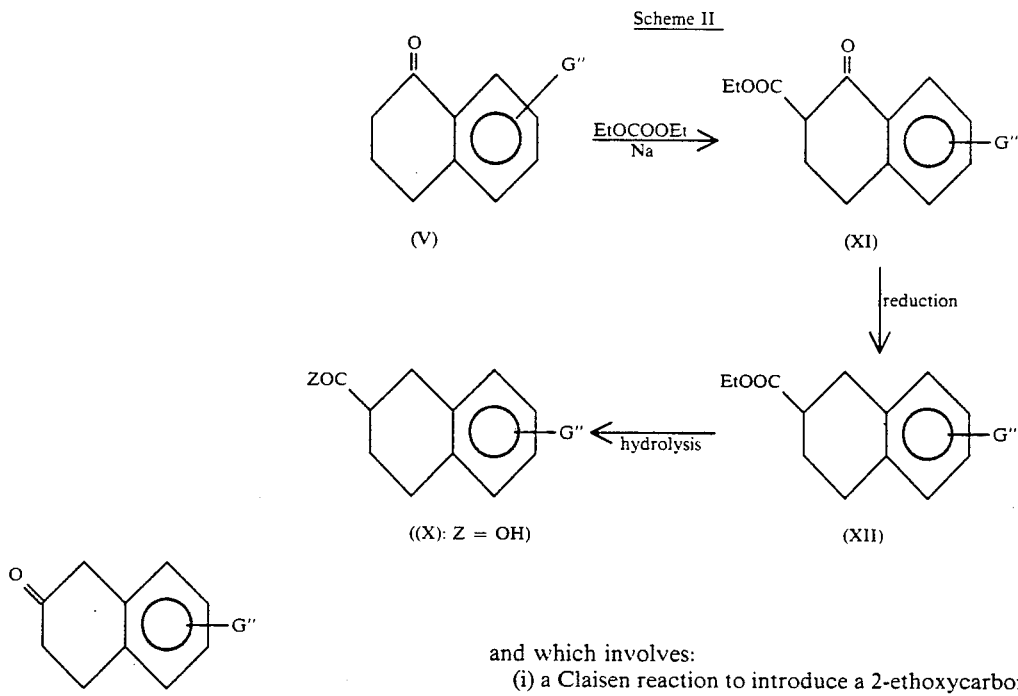

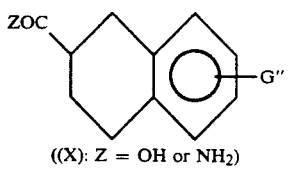

((X): Z = OH or NH₂)

through reaction with an at least equimolar amount of an alkali metal cyanide, typically sodium cyanide, in an aprotic, preferably polar, organic solvent, e.g. dimethylsulfoxyde or dimethylformamide. Said reaction which may be carried out at a temperature comprised between room temperature and the reflux temperature of the reaction mixture, directly affords the compound of formula (VIII) which is then further processed as described in Scheme I. If desired, the thus obtained racemates of formula (III) may be separated into their pure isomers by formation of diastereoisomeric salts with optically active organic acids such as camphorsulfonic acids, optionally substituted mandelic acids or other optically active acids.

If the aminomethyltetralin (III) contains a second chiral centre, the diastereoisomers and the four pure isomers can be isolated as described above. They can then be employed for the preparation of all the possible isomers of the compounds of formula (I).

According to another useful method of preparation of the compounds of formula (III), there may be employed as starting compounds the corresponding carboxylic acids of formula (X) wherein Z is a hydroxy group These products are converted into the corresponding amides ((X): Z=NH₂), and the amido group is then transformed into aminomethyl.

The above acids of formula (X) wherein Z is a hydroxy group may be prepared from the corresponding and which involves:
(i) a Claisen reaction to introduce a 2-ethoxycarbonyl group in the 1-tetralone (V), through reaction with diethylcarbonate in the presence of sodium,
(ii) reduction of the 1-oxo group of the compound of formula (XI), either catalytically with H₂ in the presence of Pd/C, or chemically with triethylsilane/trifluoroacetic acid (Tetrahedron, 1967, 23, 2235), or with triethylsilane/BF·Et₂O (J.Org.-Chem., 1985, 50, 3619) or, again, with triethylsilane/trifluoromethanesulfonic acid (Synthesis, 1986, 779), and
(iii) saponification of the ester (XII).

Conversion of the acids into the corresponding amides of formula ((X): Z=—NH₂) is carried out by the conventional methods which involve nucleophilic addition of ammonia on the positively polarised carbon of the acid functional derivative.

As acid functional derivatives there may be employed acyl chlorides, anhydrides, mixed anhydrides, active esters or suitably activated free acids, e.g. with DCCI or BOP.

Reduction of the amido group is usefully achieved by way of for instance, hydride reduction e.g. with lithium aluminum hydride or diborane, typically borane-methyl sulfide. The reaction is carried out in the presence of an aprotic organic solvent, such as a cyclic or linear ether, typically dioxane or tetrahydrofuran.

The thus obtained compounds of formula (III) wherein G=G" and represents hydrogen, chloro, hydroxy or methoxy, may be converted into the other compounds of formula (III) as described above.

Starting from the acid of formula ((X): Z —OH), in optically active form, the compound of formula (III) with the same absolute configuration at the chiral carbon is obtained.

The optically active acids of formula (X) may be obtained starting from the corresponding racemates by formation of diastereoisomeric salts thereof with optically active amines such as d-α-methylbenzylamine, l-α-methylbenzylamine, d-menthylamine, and l-menthylamine and precipitation of said salts from a suitably selected solvent.

The acids and the amides of formula (X) in optically pure forms are new compounds which allow an easy preparation of the optically pure isomers (I) and represent therefore a further specific object of the present invention.

The compounds of formula (I) and their salts possess very interesting pharmacological properties as they showed to be active as intestinal motility modulating agents.

In particular, their effects in reducing colon spontaneous motility have been observed in in vitro normalized pharmacological tests and has been confirmed in the animal in vivo.

In the in vitro tests, the capability of different concentrations of the phenylethanolaminomethyltetralins of the present invention to reduce, under particular normalised conditions, the spontaneous contractile activity of isolated proximal colon rat strips has been evaluated.

Not fasted male rats weighing 250-300 g are sacrificed. The proximal part of the colon, approximately a 2 to 3 cm segment, is removed and suspended in a 20-ml organ bath containing oxygenated (5% $CO_2$, 95% $O_2$) Krebs-Ringer solution with the following mM composition: NaCl 118.4; KCl 4.7; $CaCl_2$ 2.45; $MgSO_4$ 1.16; $NaH_2PO_4$ 3.7; glucose 5.6; $NaHCO_3$ 30.9, kept at a constant temperature of 37° C. The colon strips submitted to a 1 g traction spontaneously contract. The test compounds are added thereto after stabilisation of the preparation (2h).

The $EC_{50}$, i.e. the concentration which is effective to reduce by 50% the contractile activity observed in controls, is determined.

In this test the compounds of the present invention showed a very high activity characterised, for the most active compounds, by $EC_{50}$s in the range of from 1 to 50 nM.

The compounds of formula (I) showed also a surprising specificity towards the colon. In vitro tests, carried out by the same general method but on isolated rat uterus, showed that a significative effect on spontaneous uterus motility is obtained at doses much higher than those active on colon.

With regard to the compounds described in European Patent EP-B-211,721, the compounds of formula (I) of the present invention showed to be more potents and more selectives.

As an example, the compound of Example 4 (N-[(7-methoxy-1,2,3,4-tetrahydronaphth-2-yl)methyl]-2-hydroxy-2-(3-chlorophenyl)ethanamine hydrochloride) is characterised by an $EC_{50}$, on colon, of 43 nM and an $EC_{50}$, on uterus, of 2,453 nM corresponding to a selectivity ratio of 57, whereas the compound described in Example 7 of EP-B-211,721 (N-(7-methoxy-1,2,3,4-tetrahydronaphth-2-yl)-2-hydroxy-2-(3-chlorophenyl)ethanamine hydrochloride) is characterised by an $EC_{50}$, on colon, of 194 nM and an $EC_{50}$, on uterus, of 350 nM (selectivity ratio lower than 2).

Also, the compound of Example 10, as the hydrochloride, is characterised by an $EC_{50}$, on colon, of 7 nM and an $EC_{50}$, on uterus, of 50 nM (selectivity ratio of about 7), while the compound described in Example 8 of EP-B-211,721, which structurally differs therefrom in the absence of the —$CH_2$— group between the tetralin moiety and the —NH— group, is characterised by an $EC_{50}$ of 110 nM both on colon and uterus (selectivity ratio=1).

In the in vivo tests, intestinal motility in the anesthetized rat by the method described in EPA-255,415 has been evaluated. The compounds of the present invention have shown a very good activity at very low doses.

The phenylethanolaminomethyltetralins of formula (I) and their pharmaceutically acceptable salts have also a very low toxicity, compatible with the utilization of these products as drugs.

Thus, in another of its embodiments, the present invention concerns the pharmaceutical compositions mainly useful in the treatment of intestinal troubles comprising, as the active principle, one or more compounds of formula (I) or their pharmaceutically acceptable salts.

In the pharmaceutical compositions of the present invention suitable for oral, sublingual, subcutaneous, intramuscular, intravenous, trans-dermal, or rectal administration, the above active principles may be administered, in unit dosage forms in admixture with the conventional pharmaceutical carriers, to mammals for the treatment of intestinal motility troubles. Suitable unit dosage forms comprise the oral forms such as tablets, capsules, powders, granules, and the solutions and suspensions for oral administration, the sublingual and buccal forms, the subcutaneous, intramuscular, intravenous, and rectal forms.

To achieve the desired therapeutical effect, the daily dosage of active principle may vary from 0.01 to 100 mg/kg of body weight. Each unit dose may contain from 0.1 to 500 mg of active principle in admixture with a suitable pharmaceutical carrier. Said unit dosage form may be administered from 1 to 4 times a day.

When a solid composition is prepared in tablet form, the main active ingredient is mixed with a pharmaceutical carrier such as gelatine, starch, lactose, magnesium stearate, talc, arabic gum, and the like. Tablets may be coated with sucrose or other suitable materials or they may be treated so that their activity is extended or delayed and that they continually release a predetermined amount of active principle.

A preparation in capsules is obtained by mixing the active ingredient with a diluent and a lubricant and by filling soft or hard capsules with the thus obtained mixture.

A liquid preparation in the form of syrup or elixir or for the administration in drops may contain the active ingredient jointly with a possibly acaloric sweetener, methylparaben, and propylparaben as antiseptics, as well as a flavoring agent and a suitable dye.

Water-dispersible powders or granules may contain the active ingredient mixed with dispersing agents or wetting agents, or suspending agents, such as polyvinylpyrrolidone and the like agents, and with sweetening or flavoring agents.

For rectal administration suppositories are prepared with binding agents melting at rectal temperature, for example cocoa butter or polyethyleneglycols.

For parenteral administration, aqueous suspensions, isotonic saline solutions or sterile injectable solutions are employed which contain pharmacologically compatible dispersing and/or wetting agents, for example propyleneglycol or butyleneglycol.

The active principle may also be formulated in the form of microcapsules or microemulsions, possibly with one or more supports or additives.

The main active principle of formula [I] may be administered as the free base or as a pharmaceutically acceptable salt thereof, as such or as a complex with, for instance, a dextrine, or even in association or co-administration with other active principles, such as tranquillisers.

The compounds of formula (I) and their salts are also active in controlling high intraocular pressure, i.e. in normalizing, reducing and modulating high intraocular pressure. They can therefore be employed in the treatment of ocular hypertension and glaucoma, an ocular disorder which leads to a damage of the optical nerve fibers and may ressort in loss of the visual function, which is characterised, among other symptoms, by an increase in intraocular pressure.

The high ocular pressure lowering effect of the compounds of formula (I) as well as of their salts may be evaluated in animals, as an example in the rabbit, by means of a test which involves oral administration of large amounts of water, such as that described in Arch. Ophthal., 1969, 82,381–384, or in J. Ocul. Pharmacol., 1985, 1(2), 161–168; or rapid i.v. injection of a glucose solution, such as that described in Boll. Ocul., 1979, 58(7–8), 359–66.

The present invention, therefore, also concerns, in still another embodiment thereof, an ophthalmic pharmaceutical composition to be administered topically to the eye, which comprises a phenylethanolaminomethyl-tetralin of formula (I) or a pharmaceutically acceptable salt thereof.

The ophthalmic compositions according to the present invention, as solutions, suspensions, or ointments, may contain from 0.00001 to 1% by weight, more particularly from 0.0001 to 0.2%, of a compound of formula (I) or a pharmaceutically acceptable salt thereof.

Each dosage unit (drop) contains from 10 ng to 1 mg, and preferably from 100 ng to 0.2 mg of a phenylethanolaminomethyltetralin. These preparations may be administered by applying, in the eye, 1 or 2 drops, 1 to 3 times a day, to provide a daily posology of from 10 ng to 1 mg, and preferably from 100 ng to 0.2 mg, of active principle.

To obtain suitable preparations, the phenylethanolaminomethyltetralins of the invention may be admixed with a carrier acceptable for a topical ophthalmic administration. As pharmaceutical acceptable carriers for an ophthalmic topical administration, there may be cited water, mixtures of water and water-miscible solvents, such as lower alkanols, vegetable oils, mineral oils which may contain from 0.5 to 5% by wt. of hydroxyethylcellulose, ethyl oleate, carboxymethylcellulose, polyvinylpyrrolidone, and other water-soluble polymers, which are non toxic and compatible with an ophthalmic use, as an example cellulose derivatives, such as methylcellulose, carboxymethylcellulose alkali metal salts, hydroxymethylcellulose, hydroxyethyl cellulose, hydroxypropylmethylcellulose, acrylates such as polyacrylic acid salts, ethylpolyacrylates, polyacrylamides, natural products such as gelatin, alginates, pectines, tragacanth, karaya gum, chondrus, agar, acacia, starch derivatives, such as starch acetate, hydroxyethyl starch ethers, hydroxypropyl starch, as well as other synthetic derivatives such as polyvinylalcohol, polyvinylpyrrolidone, polyvinylmethyl ether, polyethylene oxide, neutral carbopol, or xanthan, and their mixtures. The pharmaceutical preparations may also contain non-toxic auxiliary substances such as emulsifying, preserving, wetting, bodying agents and the like such as for instance polyethyleneglycols 200, 300, 400, 600, carbowaxes 1,000, 1,500, 4,000, 6,000, 10,000, antibacterial agents such as quaternary ammonium compounds, phenylmercuric salts known to have cold sterilising properties and which are non-injurious in use, thimerosal, propylparaben, benzyl alcohol, phenylethanol, buffering agents, such as alkali metal chlorides, borate, acetate or gluconate buffers, antioxidants such as sodium metabisulfite, butylated hydroxyanisole, butylated hydroxytoluene, or the like agents, and other agents typically used in this field such as sorbitan monolaurate, triethanolamine oleate, polyoxyethylene sorbitan monopalmitate, dioctyl alkali metal sulfosuccinate, monothioglycerol, ethylenediamine tetraacetic acid and the like.

Additionally, suitable ophthalmic excipients may be employed such as for instance phosphate buffer, isotonic boric acid, isotonic alkaline chloride solutions or tromethamine.

The pharmaceutical preparation may also be in the form of a suspension wherein the soluble particles are water-soluble or insoluble polymers. Such suspensions may contain microparticles or nanoparticles.

The compositions according to the present invention may contain additional active principles. Accordingly, antibiotics, anesthetics, steroid or costicosteroid antiinflammatory agents which are suited for the treatment of glaucoma, but provoke as a side effect an increase in intraocular pressure, or other high ocular pressure lowering agents, may be present.

The following examples further illustrate the invention without limiting it. The solvents indicated between parentheses after the melting point represent the crystallisation solvents The rotatory power which is conventionally indicated as [α], should actually read as $[\alpha]_D^{20}$.

Preparation of the starting compounds of formula (III)

Preparation (A)

2-aminomethyl-5-methoxy-1,2,3,4-tetrahydronaphthalene hydrochloride 2-cyano-5-methoxy-1,2,3,4-tetrahydro-1-nalphthol is prepared by the method described in literature for the 6-methoxy compound (Synthesis, 1981, 449–451), which is summarized in following steps (i) to (iv), and then converted into 2-aminomethyl-5-methoxy-1,2,3,4-tetrahydronaphthalene hydrochloride by the method described in details in steps (v) and (vi).

(i) 2-formyl-5-methoxy-3,4-dihydronaphthalen-1(2H)-one

A solution of ethyl formate (20 ml, 0.37 mol) in anhydrous benzene (100 ml) is added to sodium ethoxide, prepared from sodium (8.34 g, 0.35 mol) and absolute ethanol, in anhydrous benzene (100 ml). The reaction mixture is cooled to about 0° C. and a solution of 5-methoxy-3,4-dihydronaphthalen-1(2H)-one (25 g, 0.14 mol) in anhydrous benzene (100 ml) is then slowly stirred in. By working up the mixture as described in J. Am. Chem. Soc., 1947, 69, 2942, the above indicated product is recovered (24.8 g); m.p. 68°–70° C.

(ii) 6-methoxy-4,5-dihydronaphth[2,1-d]isoxazole

A mixture of the product obtained in step (i) (23.8 g, 0.11 mol) and hydroxylamine hydrochloride (8.2 g, 0.12 mol) in methanol (300 ml) is refluxed for ten minutes and then evaporated off under vacuum. Water is added thereto and the mixture is extracted with ethyl ether affording 19 g of the compound indicated in the title; m.p. 84°–86° C.

(iii) 2-cyano-5-methoxy-3,4-dihydronaphthalen-1(2H)-one

The compound obtained in the preceding step (19 g, 0.094 mol) is treated for 1 hour, at about 0° C., with sodium methoxide prepared from sodium (4.7 g, 0.188 mol) and anhydrous methanol (250 ml). The reaction mixture is evaporated under vacuum, water is added thereto and the product is extracted with ethyl acetate yielding 16.7 g of the compound indicated in the title; m.p. 120°–122° C.

(iv) 2-cyano-5-methoxy-1,2,3,4-tetrahydro-1-naphthol

The compound obtained in step (iii) above (16.2 g, 0.080 mol) is reduced with sodium borohydride (3.1 g, 0.082 mol) in absolute methanol (500 ml). The reaction mixture is concentrated under vacuum, ice-water is added thereto, the mixture is made acidic by the addition of concentrated hydrochloric acid and extracted with ethyl acetate. Upon evaporation of the solvent 2-cyano-5-methoxy-1,2,3,4-tetrahydro-1-naphthol (16.2 g) is obtained; m.p. 96°–98° C.

(v) 2-cyano-5-methoxy-3,4-dihydronaphthalene

A mixture of the compound obtained in step (iv) above (16.2 g, 0.079 mol) and POCl (30 ml, 0.32 mol) in pyridine (200 ml) is heated for 3 hours to 120° C. ext.. The reaction mixture is then cooled and made acidic by the dropwise addition of 2N HCl. The solution is treated with ethyl acetate, the organic phase is recovered, washed with a saturated sodium bicarbonate solution and then with water. The organic phase is dried over sodium sulfate, filtered and concentrated to dryness yielding the compound indicated in the title [9.8 g]; m.p. 47°–49° C. (isopropyl ether).

(vi) 2-aminomethyl-5-methoxy-1,2,3,4-tetrahydronaphthalene hydrochloride

A solution of the compound obtained in step (v) above (9.2 g, 0.05 mol) in anhydrous tetrahydrofuran (150 ml) is added dropwise to a mixture of lithium aluminum hydride (3.8 g, 0.1 mol) and anhydrous tetrahydrofuran (50 ml) under nitrogen atmosphere. The reaction mixture is heated to the reflux temperature for 4 hours, and then cooled. Water (40 ml) is added thereto and the reaction mixture is extracted with ethyl acetate (2×300 ml). The organic phase is dried over sodium sulfate, filtered and concentrated to dryness. The residue is then purified by flash chromatography eluting with methanol/ammonia 97/3. The hydrochloride is prepared by treating the thus obtained free base with HCl saturated isopropanol. The product of the title (9 g) is thus obtained; m.p.231°–232° C. (ethanol).

Preparation (B)

2-aminomethyl-6-methoxy-1,2,3,4-tetrahydronaphthalene hydrochloride

The above compound is obtained by following the procedure described in Preparation (A) but starting from 6-methoxy-3,4-dihydronaphthalen-1-one instead of 5-methoxy-3,4-di-hydronaphthalen-1-one; m.p. 222°–224° C. (ethanol).

Preparation (C)

2-aminomethyl-8-methoxy-1,2,3,4-tetrahydronaphthalene hydrochloride

Trimethylsylyl cyanide (6.9 g, 9.3 ml, 0.07 mol) is added dropwise in 10 minutes to a mixture of 8-methoxy-3,4-di-hydronaphthalen-2(1H)-one (10.9 g, 0.06 mol) prepared as described in the literature (J. Chem. Soc., 1958, 409), anhydrous acetonitrile (60 ml) and a catalytic amount of zinc iodide under nitrogen atmosphere and the obtained mixture is heated to 80° C. ext. for 3 hours. The reaction mixture is cooled, 1N HCl (20 ml) is slowly added thereto and stirring is continued for 2 hours at room temperature. The solvent is then evaporated off under vacuum, the residue is taken up in ethyl acetate, and the organic solution is washed with water, dried over sodium sulfate, filtered and evaporated to dryness. The obtained product is triturated with petroleum ether, filtered and dissolved in pyridine (100 ml). POCl$_3$ (20 ml) is added dropwise in 10 minutes and the obtained mixture is heated to 120° C. ext. for 3 hours. The reaction mixture is then poured into ice, made acidic by the addition of concentrated hydrochloric acid and extracted with ethyl ether. The organic phase is washed with water, dried and evaporated to dryness and the obtained residue is crystallised from isopropyl ether yielding 2-cyano-8-methoxy-3,4-dihydronaphthalene (7.2 g); m.p. 66°–68° C.

The thus obtained product is hydrogenated at room temperature and atmospheric pressure in 95% ethanol (100 ml) using 5% Pd/C as the catalyst. When the theoretical amount of hydrogen has been consumed, the reaction mixture is filtered, the filtrate is concentrated under reduced pressure, the residue is triturated with petroleum ether and recovered by filtration affording 2-cyano-8-methoxy-1,2,3,4-tetrahydronaphthalene (7 g); m.p. 66°–68° C.

Said product is dissolved in anhydrous tetrahydrofuran (30 ml) and the thus obtained solution is then added to a suspension of lithium aluminum hydride (1.5 g, 0.04 mol) in anhydrous tetrahydrofuran (20 ml). The reaction mixture is refluxed for 4 hours, then cooled to room temperature and treated with water first and then with ethyl acetate. The organic phase is separated and treated with diluted hydrochloric acid. The acidic aqueous phase is separated, made basic by the addition of ammonia water, and extracted with ethyl acetate. The organic extract is washed with water, dried, and evaporated to dryness. The obtained residue is taken up in isopropanol and 2-aminomethyl-8-methoxy-1,2,3,4-tetrahydronaphthalene hydrochloride (2.49 g) is then precipitated therefrom by the addition of HCl saturated isopropanol. M.p. 210°–212° C. (isopropanol).

Preparation (D)

2-aminomethyl-8-hydroxy-1,2,3,4-tetrahydronaphthalene hydrobromide

A mixture of the compound obtained in Preparation (C) above (3 g, 0.013 mol) and 48% aqueous HBr (50 ml) is refluxed for 4 hours, and then evaporated to dryness under vaccum. The obtained residue is taken up in absolute ethanol (3×50 ml) each time evaporating off the solvent. The residue is triturated with acetone, filtered and washed with acetone and then with ethyl ether thus yielding 2.8 g of the compound of the title. M.p. 233°–235° C. (isopropanol).

Preparation (E)

2-aminomethyl-5-hydroxy-1,2,3,4-tetrahydronaphthalene hydrobromide

The compound of the title is prepared by following the procedure of the foregoing Preparation but starting from the compound of Preparation (B). M.p. 212°–214° C. (ethanol).

Preparation (F)

2(S)-aminomethyl-7-methoxy-1,2,3,4-tetrahydronaphthalene hydrochloride (i) 7-methoxy-1,2,3,4-tetrahydronaphthalen-2(S)-carboxylic acid (R)-(+)-α-methylbenzylamine (25.8 ml, 0.2 mol) is added to a solution of 7-methoxy-1,2,3,4-tetrahydronaphthalen-2-carboxylic acid racemate (41 g, 0.2 mol) in acetone (800 ml) and after 2 hours at room temperature the obtained salt is recovered by filtration (45.2 g) and crystallized twelve times from acetone until a product with constant $[\alpha]$ of $-20.5°$ (c=1.4%, CHCl$_3$) is obtained. This product is then taken up in water (30 ml) and the obtained solution is made acidic by the addition of concentrated HCl and extracted with ethyl ether. The organic phase is dried and evaporated to dryness and the obtained residue is crystallised from benzene (20 ml) affording 0.9 g of 7-methoxy-1,2,3,4-tetrahydronaphthalen-2(S)-carboxylic acid; m.p. 133°–135° C.; $[\alpha]=-45.1°$ (c=1.4%, CHCl$_3$). To determine its absolute configuration, the thus obtained product is converted into the corresponding 2-amino-7-methoxy-1,2,3,4-tetrahydronaphthalene by the Curtius reaction.

The $[\alpha]$ of the thus obtained 2-amino-7-methoxy-1,2,3,4-tetrahydronaphthalene corresponds to that of the 2(S) isomer which is described in EP-A-303,545. As the priority arrangement of the ligands attached to the asymmetric carbon of 2-amino-7-methoxy-1,2,3,4-tetrahydronaphthalene is identical to that of 7-methoxy-1,2,3,4-tetrahydronaphthalene-2-carboxylic acid and the Curtius reaction is stereoconservative, (S) absolute configuration can correctly be attributed to the thus obtained 7-methoxy-1,2,3,4-tetrahydronaphthalen-2-carboxylic acid.

(ii) 7-methoxy-1,2,3,4-tetrahydronaphthalen-2(S)-carboxamide

A solution of triethylamine (10.2 ml, 0.072 mol) in acetone (50 ml) is added in 15 minutes to a solution of the acid obtained in step (i) (10.8 g, 0.052 mol) in acetone (200 ml) cooled to $-10°$ C. A solution of ethyl chloroformate (7.9 ml, 0.080 mol) in acetone (80 ml is then added thereto and after 1.5 hours at $-10°$ C., concentrated ammonia water (16.6 ml, 0.133 mol) is dripped in. The reaction mixture is then kept at $-10°$ C. for 1 hour and at room temperature for 3 hours. Acetone is evaporated off, the residue is taken up in ethyl acetate (500 ml) and the obtained solution is washed sequentially with water, a sodium bicarbonate solution, 6N hydrochloric acid, and water. Then it is dried and evaporated to dryness. The residue is triturated in isopropyl ether and filtered yielding the amide of the title (9.5 g), m.p. 159°–161° C. (ethyl acetate); $[\alpha]=-52.2°$ (c=1.4%, CHCl$_3$). Enantiomeric excess: 96.5%.

(iii) 2(S)-aminomethyl-7-methoxy-1,2,3,4-tetrahydronaphthalene hydrochloride

A solution of the compound obtained in step (ii) above (9.5 g, 0.046 mol) in anhydrous tetrahydrofuran (167 ml) is heated to the reflux temperature under nitrogen atmosphere and 10M borane-dimethylsulfide (14.2 ml, 0.142 mol) in anhydrous tetrahydrofuran (60 ml) is then dripped in. The reaction mixture is refluxed for 4 hours and then cooled to 0°–5° C. Methanol (95 ml) is slowly added thereto, the solution is refluxed for 1 hour and then evaporated to dryness. The residue is taken up in 1N sodium hydroxide and the obtained solution is then extracted with ethyl acetate. The organic phase is washed with water, dried and evaporated to dryness The obtained residue is purified by flash chromatography eluting with a mixture methanol/ammonia 98/2. The thus obtained product is dissolved in isopropanol (30 ml) and hydrogen chloride saturated isopropanol is then added thereto to precipitate the compound of the title (5.3 g); m.p. 228°–230° C.; $[\alpha]=-80.4°$ (c=1.4%, MeOH).

The starting 7-methoxy-1,2,3,4-tetrahydronaphthalen-2-carboxylic acid, which is a known product, can be prepared as follows: a solution of 7-methoxy-3,4-dihydronaphthalene-1(2H)-one (66.4 g, 0.376 mol) in anhydrous tetrahydrofuran (350 ml) is added in 1 hour to a mixture of distilled diethylcarbonate (116 ml, 0.957 mol), 80% sodium hydride (39.7 g, 1.32 mol) and anhydrous tetrahydrofuran (350 ml) heated to 60° C. The thus obtained reaction mixture is refluxed for 4 hours and then cooled. Acetic acid is then added dropwise up to acidic pH and water is added until complete dissolution of the precipitate occurs. The solution is extracted with ethyl ether, the organic phase is washed with water and with a sodium bicarbonate solution, dried and evaporated to dryness. The thus obtained oily product is purified by distillation under reduced pressure yielding 90 g of 7-methoxy-1-oxo-1,2,3,4-tetrahydronaphthalen-2-carboxylic acid ethyl ester. B.p.$_{0.4}$ $_{mmHg}$ 160°–165° C.

The thus obtained product is dissolved in a mixture of glacial acetic acid (600 ml) and 70% perchloric acid (4 ml) and is hydrogenated at room temperature and atmospheric pressure for 3 hours using 10% Pd/C as the hydrogenation catalyst. The mixture is then filtered on celite, the filtrate is poured into water (4500 ml) and extracted with ethyl acetate. The organic phase is washed with water and then with a sodium bicarbonate saturated solution, then it is dried over sodium sulfate, filtered and concentrated to dryness yielding an oily product which is distilled at 0.3 mmHg and 130° C. 7-methoxy-1,2,3,4-tetrahydronaphthalen-2-carboxylic acid ethyl ester (65.8 g) is thus obtained.

A mixture of the thus obtained ester (159.5 g, 0.68 mol) and sodium hydroxide (29.9 g, 0.75 mol) in water (600 ml) and 95% ethanol (600 ml) is refluxed for 2 and ½ hours. Ethanol is evaporated off, the solution is made acidic by the addition of concentrated hydrochloric acid and extracted with ethyl acetate. The organic extract is dried over sodium sulfate, filtered and evaporated to dryness thus yielding 7-methoxy-1,2,3,4-tetrahydronaphthalen-2-carboxylic acid which is then crystallised from isopropyl ether. M.p. 125°–127° C.

Alternatively, compound (F) may also be obtained starting from the racemate by the following method:

(i′) A solution of L (+)-mandelic acid (11.93 g, 0.078 mol) in methanol (100 ml) is added to a solution of 2-aminomethyl-7-methoxy-1,2,3,4-tetrahydronaphthalene (15 g, 0.078 mol) in methanol (100 ml).

The precipitate is separated from the mother liquors by filtration and it is recrystallised seven times from methanol thus affording a compound characterised by $[\alpha]=-31.4°$ (c=1.4%, MeOH).

(ii′) The salt is taken up in 0.1 N HCl, and the obtained solution is then extracted with ethyl acetate. The aqueous phase is made basic by the addition of a sodium carbonate solution and extracted with ethyl acetate. This last organic extract is then dried and evaporated to dryness to afford a residue which is dissolved in isopropanol. The compound of the title is then precipitated therefrom by the addition of hydrogen chloride saturated isopropanol and is recovered by filtration M.p. 228°-230° C.; [α]= −79.0° (c=1.4%, MeOH).

Preparation (G)

2(R)-aminomethyl-7-methoxy-1,2,3,4-tetrahydronaphthalene hydrochloride (i) 7-methoxy-1,2,3,4-tetrahydronaphthalen-2(R)-carboxylic acid The mother liquors from salt precipitation as well as first and second crystallisations described in Preparation (F)(i) are combined and evaporated to dryness. Hydrochloric acid is added to the residue and the solution is extracted with ethyl ether. The organic phase is evaporated to dryness, affording 7-methoxy-1,2,3,4-tetrahydronaphthalen-2-carboxylic acid (26 g, 0.126 mol). Said acid is dissolved in acetone (250 ml) and (S)-(-)-α-methylbenzylamine (16.3 ml, 0.126 mol) is added to the thus obtained solution. After 2 hours at room temperature the mixture is filtered and the precipitated salt is recovered (33.5 g). Said salt is crystallised ten times from acetone then it is taken up in water (30 ml), the aqueous solution is made acidic by the addition of concentrated hydrochloric acid and extract-ed with ethyl ether. The organic phase is dried, filtered and evaporated to dryness affording 7-methoxy-1,2,3,4-tetrahydronaphthalen-2(R)-carboxylic acid (1 g). M.p. 133°-135° C. (benzene); [α]= +44.6° (c 32 1.4%, CHC$_3$).

The above acid is then converted into 2-amino-7-methoxy-1,2,3,4-tetrahydronaphthalene hydrochloride by the method described in Preparation (F)(i). A product is obtained which is characterised by [α]= +66.6° (c=0.5%, MeOH) that corresponds to the [α] value of 2(R)-amino-7-methoxy-1,2,3,4-tetrahydronaphthalene (Molecular Pharmacology, 1982, 22, 281). The absolute configuration of the above compound is thus confirmed.

(ii) 7-methoxy-1,2,3,4-tetrahydronaphthalen-2(R)-carboxamide

This compound (9.5 g) is obtained following the procedure described in Preparation (F)(ii) but starting from 7-methoxy-1,2,3,4-tetrahydronaphthalen-2(R)-carboxylic acid (10.8 g, 0.052 mol). M.p. 157°-159° C. (ethyl acetate); [α]= +52.7° (c=1.4%, CHC$_3$). Enantiomeric excess: 94%.

(iii) 2(R)-aminomethyl-7-methoxy-1,2,3,4-tetrahydronaphthalene hydrochloride

Following the same procedure of Preparation (F)(iii) but starting from 7-methoxy-1,2,3,4-tetrahydronaphthalen-2(R)carboxamide (9 g, 0.044 mol), the compound of the title (5.5 g) is obtained; m.p. 229°-231° C. (isopropanol); [α]= +83.6° C. (c=1.4%, MeOH).

Alternatively, compound (G) may also be obtained starting from the mother liquors of salt precipitation as well as first and second crystallisation described in alternative Preparation (F)(i') according to the following method: the methanol solution is evaporated to dryness, the residue is taken up in 1N hydrochloric acid and the obtained solution is washed with ethyl acetate. The aqueous solution is made basic by the addition of 1N NaOH and extracted with ethyl acetate. The organic phase is dried and concentrated to dryness, the thus obtained residue is dissolved in methanol and an equimolar amount of D(−)-mandelic acid is added thereto. The precipitate which forms is recovered by filtration and crystallised from methanol seven times thus affording a product with [α]= +31.8° (c=1.4%, MeOH).

The thus obtained salt is dissolved in 0.1N hydrochloric acid and the solution is extracted with ethyl acetate. The aqueous solution is then made basic by the addition of aqueous Na$_2$CO$_3$ and extracted with ethyl acetate. The organic phase is dried and evaporated to dryness. The residue is dissolved in isopropanol and HCl saturated isopropanol is then added thereto to precipitate compound (G). M.p. 228°-230° C.; [α]= +83.1° (c=1.4%, MeOH).

Preparation (H)

2(R)-aminomethyl-7-hydroxy-1,2,3,4-tetrahydronaphthalene

A solution of the compound obtained in Preparation (G) (5 g, 0.022 mol) in 48% aqueous hydrobromic acid (100 ml) is refluxed for 5 hours, and then it is evaporated to dryness. The residue is taken up in concentrated ammoniun hydroxide (30 ml), the solution is extracted with ethyl acetate (4×200 ml) and the organic extracts are combined, dried, filtered and concentrated to dryness. Crystallisation of the residue from isopropanol (80 ml) affords the compound indicated in the title (2.4 g). M.p. 192°-194° C.; [α]= +116.78° (c=1%, MeOH).

Preparation (I)

2(S)-aminomethyl-7-hydroxy-1,2,3,4-tetrahydronaphthalene

The above compound (2.9 g) is obtained by following the procedure of Preparation (H) but starting from the compound obtained in Preparation (F) (5 g, 0.022 mol); m.p. 191°-193° C. (isopropanol); [α]= −106.5° (c=1%, MeOH).

Preparation (J)

2-aminomethyl-6-hydroxy-1,2,3,4-tetrahydronaphthalene

The above compound is obtained by following the procedure of Preparation (H) but starting from the compound obtain in Preparation (B). M.p. 181°-183° C. (isopropanol).

Preparation (K)

Ethyl [(2-aminomethyl-1,2,3,4-tetrahydronaphth-7-yl)oxy]acetate hydrochloride (i) 7-hydroxy-2-(N-tertbutoxycarbonyl)aminomethyl-1,2,3,4-tetrahydronaphthalene 2-aminomethyl-7-methoxy-1,2,3,4-tetrahydronaphthalene is obtained by the process described in Preparation (A), but starting from 7-methoxy-3,4-dihydronaphthalen-1-one, and is treated with aqueous hydrobromic acid according to the procedure described in Preparation (H). A suspension of the thus obtained 2-aminomethyl-7-hydroxy-1,2,3,4-tetrahydronaphthalene (6 g, 0.034 mol) in dimethylformamide (89 ml) and triethylamine (4.7 ml, 0.034 mol) is stirred at room temperature for 10 minutes and 90% di-tert-butyl-dicarbonate (8.2 g, 0.034 mol) is then added thereto. The reaction mixture is stirred at room temperature for 3 hours and then poured into water (about 400 ml) and the obtained solution is extracted with ethyl acetate. The organic phase is washed with water, dried over sodium sulfate, filtered and evaporated to dryness affording an oily product which is purified by flash chromatography eluting with a mixture ethyl acetate/cyclohexane 2/8.

The residual oil is pumped to dryness under reduced pressure thus yielding a vitreous solid. IR (KBr):3364 (b): O—H, CON—H; 1690: =OC ONH cm$^{-1}$.

(ii) Ethyl [(2-(N-tertbutoxycarbonyl)aminomethyl-1,2,3,4-tetrahydronaphth-7-yl)oxy]acetate A mixture of the above product (3.4 g, 0.009 mol), powdered potassium carbonate (4 g, 0.09 mol) and acetone (100 ml) is stirred at room temperature for 30 minutes and then ethyl bromoacetate (4.56 g, 3 ml, 0.027 mol) is added thereto. The reaction mixture is refluxed for 5 hours, filtered and concentrated under vacuum. The residue is dissolved in ethyl ether, the solution is washed with water, dried over sodium sulfate and evaporated to dryness under reduced pressure. The obtained product is triturated with isopropyl ether and filtered thus affording ethyl [(2-(N-tertbutoxy -carbonyl)aminomethyl-1,2,3,4-tetrahydronaphth-7-yl)oxy]acetate (m.p. 94°-97° C.).

(iii) Ethyl [(2-aminomethyl-1,2,3,4-tetrahydronaphth-7-yl)oxy]acetate hydrochloride A mixture of the product obtained in step (ii) above (2.1 g, 0.0058 mol) and absolute ethanol (15 ml) is cooled to about 0° C. and 7.2N hydrogen chloride in ethanol (5 ml) is then added thereto. When the addition is terminated, the reaction mixture is heated to about 50° Cfor 30 minutes and then concentrated to dryness under vacuum. The obtained residue is triturated with acetone and filtered yielding 1.2 g of the compound of the title; m.p. 136°-138° C. (isopropanol).

Preparation (L)

Ethyl [(2-aminomethyl-1,2,3,4-tetrahydronaphth-7-yl)oxy]-butanoate hydrochloride A mixture of the compound obtained in Preparation (K)(i) (3.8 g, 0.013 mol), powdered potassium carbonate (4 g, 0.09 mol) and acetone (100 ml) is stirred at room temperature for 30 minutes and then ethyl 4-bromobutanoate (11.5 g, 0.06 mol) is added thereto. The reaction mixture is refluxed for 10 hours, filtered and concentrated under vacuum. The residue is dissolved in a mixture of absolute ethanol (15 ml) and 6N hydrogen chloride in absolute ethanol (25 ml). The reaction mixture is heated to about 90° C. ext. for 4 hours and then it is concentrated to dryness under vacuum. The obtained residue is triturated with acetone and filtered yielding 2.7 g of the compound of the title; m.p. 146°-148° C.

Preparation (M)

2-aminomethyl-7-hydroxy-1,2,3,4-tetrahydronaphthalene

Starting from 2-aminomethyl-7-methoxy-1,2,3,4-tetrahydronaphthalene racemate (prepared as described in EP-A-213080) and following the procedure described in Preparation (H), 2-aminomethyl-7-hydroxy-1,2,3,4-tetrahydronaphthalene is obtained; m.p. 187°-189° C. (isopropanol).

Preparation (N)

2-aminomethyl-1,2,3,4-tetrahydronaphthalene hydrochloride

The compound indicated in the title is obtained by following the procedure described in Preparation (C) but starting from 3,4-dihydronaphthalen-2(1H)-one; m.p. 228°-230° C. (ethanol).

Preparation (O)

(+) 2-aminomethyl-6-methoxy-1,2,3,4-tetrahydronaphthalene hydrochloride [(2R) or (2S)-aminomethyl-6-methoxy-1,2,3,4-tetrahydronaphthalene hydrochloride]

(i) (+) 6-methoxy-1,2,3,4-tetrahydronaphthalen-2-carboxylic acid [(2R) or (2S) 6-methoxy-1,2,3,4-tetrahydronaphthalen-2-carboxylic acid]

A solution of (R)-(+)-α-methylbenzylamine (88.3 g, 93 ml, 0.72 mol) in acetone (500 ml) is added to a solution of 6-methoxy-1,2,3,4-tetrahydronaphthalen-2-carboxylic acid racemate (150 g, 0.727 mol) in acetone (250 ml). The reaction mixture is allowed to stand at room temperature overnight, then the salt is recovered by filtration, and it is crystallised eleven times from acetone thus obtaining a compound (6.3 g) characterised by [α]= +47.7° (c=1.4%, CHCl$_3$).

The thus obtained salt is taken up in 0.1 N NaOH and the aqueous solution is washed with ethyl ether (3×30 ml) before being treated with decolorizing carbon. The reaction mixture is then filtered, and the solution is made acidic by the addition of concentrated hydrochloric acid. The thus obtained acid is recovered by filtration, washed with water and with ethyl ether, and dried in the oven, thus affording 3.3 g of optically active acid. M.p. 129°-30° C.; [α]=+47.9° (c=1.4%, CHCl$_3$).

(ii) (+) 6-methoxy-1,2,3,4,-tetrahydronaphthalen-2-carboxamide [(2R) or (2S) 6-methoxy-1,2,3,4-tetrahydronaphthalen-2-carboxamide]

A solution of triethylamine (2.7 ml, 0.019 mol) and ethyl chloroformate (2 ml, 0.021 mol) in acetone (40 ml) is added to a solution of the acid obtained in step (i) (3 g, 0.014 mol) in acetone (50 ml) cooled to −10° C. After 1,5 hours at −10° C., concentrated NH$_4$OH (4.5 ml, 0.036 mol) is added dropwise and the reaction mixture is allowed to stand at −10° C. for 1 hour and at room temperature overnight. The solution is concentrated under vacuum, ethyl acetate (150 ml) is added to the obtained residue and the solution is washed sequentially with water, a saturated sodium bicarbonate solution, 6N hydrochloric acid, and water, then it is dried and concentrated to dryness. The residue is triturated with isopropyl ether and filtered thus affording 1.7 g of the above indicated amide; m.p. 136°-138° C.; [α]= +40.2° (c=1.4%, CHCl$_3$).

(iii) (+) 2-aminomethyl-6-methoxy-1,2,3,4-tetrahydronaphthalene hydrochloride [(2R) or (2S)-aminomethyl-6-methoxy-1,2,3,4-tetrahydronaphthalene hydrochloride]

A solution of the compound of step (ii) (1.6 g, 0.0077 mol) in anhydrous tetrahydrofuran (20 ml) is refluxed under nitrogen atmosphere and a 10M solution of borane-methyl sulfide (2.3 ml, 0.023 mol) and anhydrous tetrahydrofuran (5 ml) are gradually dripped in. The reaction mixture is heated to the reflux temperature for 4 hours, methanol (5 ml) is slowly added thereto and the mixture is refluxed for one further hour. 1N HCl (10 ml) is added and the obtained mixture is refluxed for 1 hour and then concentrated under reduced pressure and made basic by the addition of ammonium hydroxide. The aqueous solution is extracted with ethyl acetate, the organic phase is washed with water, dried and evaporated. The residue is purified by flash chromatography eluting with a mixture of methanol/ammonia 98/2. The thus obtained product is dissolved in isopropanol (30 ml), the solution is filtered and HCl saturated isopropanol is added thereto. The precipitate is recovered by filtration (1.1 g); m.p. 245°-255° C.; [α]= +70.7° (c=1.4%, MeOH).

Alternatively, Compound (O) may also be prepared starting from the racemate by to the following method:

(i') A solution of L(+)-mandelic acid (11.93 g, 0.078 mol) in methanol (100 ml) is added to a solution of 2-aminomethyl-6-methoxy-1,2,3,4-tetrahydronaphthalene (15 g, 0.078 mol) in methanol (100 ml). The precipitate is separated from the mother liquors by filtration and crystallised seven times from methanol affording a compound characterised by [α]= +92.7° (c=1.4 %, MeOH).

(ii') The thus obtained salt is taken up in 0.1 N HCl, and the solution is extracted with ethyl acetate. The aqueous solution is made basic by the addition of a sodium carbonate solution and extracted with ethyl acetate which is then evaporated off. The residue is dissolved in isopropanol and hydrogen chloride saturated isopropanol is then added thereto. Compound (O) is then recovered by filtration. [α]= +76.7° (c=1.4 %, MeOH).

Preparation (P)

(+) 2-aminomethyl-6-hydroxy-1,2,3,4-tetrahydronaphthalene hydrobromide [(2R) or (2S)-aminomethyl-6-hydroxy-1,2,3,4-tetrahydronaphthalene hydrobromide]

A mixture of the compound of Preparation (O) above (0.86 g, 0.0038 mol) and aqueous 48% hydrobromic acid (15 ml) is heated to the reflux temperature for 5 hours. The solvent is evaporated off to dryness and the residue is taken up in absolute ethanol (3×15 ml) evaporating off the solvent each time. The residue is triturated with acetone and filtered affording the compound indicated in the title (0.82 g). M.p. 248°-252° C.; [α]= +61° (c=1.4%, MeOH).

Preparation (Q)

(−) 2-aminomethyl-6-methoxy-1,2,3,4-tetrahydronaphthalene hydrochloride [(2S) or (2R)-aminomethyl-6-methoxy-1,2,3,4-tetrahydronaphthalene hydrochloride]

(i) (−) 6-methoxy-1,2,3,4,-tetrahydronaphthalen-2-carboxylic acid [(2S) or (2R) 6-methoxy-1,2,3,4-tetrahydronaphthalen-2-carboxylic acid]

The mother liquors from salt precipitation, first, second, and third crystallisation described in Preparation (O)(i) are combined and evaporated to dryness. Hydrochloric acid is added to the obtained residue, and the solution is extracted with ethyl ether. The organic extract is then evaporated to dryness affording 6-methoxy-1,2,3,4-tetrahydronaphthalen-2-carboxylic acid (126 g, 0.61 mol). Said acid is dissolved in acetone (2000 ml) and a solution of (S)-(−)-α-methylbenzylamine (80.6 ml, 0.61 mol) in acetone (500 ml) is then added thereto. The precipitated salt (116 g) is recovered by filtration and crystallised ten times from acetone affording 5.6 g of a compound with [α]= −46.7° (c=1.4%, CHCl₃).

The residue is taken up in 0.1 NaOH, and the obtained solution is washed with ethyl ether (3×30 ml), and made acidic by the addition of concentrated HCl. The obtained acid is recovered by filtration, washed with water, and with petroleum ether and dried in the oven, yielding 3.37 g of the optically active acid. M.p. 129°-130° C.; [α]= −52.5° (c=1.4%, CHCl₃).

(ii) (−) 6-methoxy-1,2,3,4,-tetrahydronaphthalen-2-carboxamide [(2S) or (2R) 6-methoxy-1,2,3,4-tetrahydronaphthalen-2-carboxamide]

The above indicated amide (1.7 g) is obtained, using the same procedure as in Preparation (O)(ii) but starting from the compound obtained in step (i) above (3 g, 0.014 mol); m.p. 138°-140° C.; [α]= −45.8° (c=1.4 %, CHCl₃).

(iii) (−) 2-aminomethyl-6-methoxy-1,2,3,4-tetrahydronaphthalene hydrochloride [(2S) or (2R)-aminomethyl-6-methoxy-1,2,3,4-tetrahydronaphthalene hydrochloride]

The compound indicated in the title (1 g) is obtained by following the procedure described in Preparation (O)(iii) but starting from (−) 6-methoxy-1,2,3,4-tetrahydronaphthalen-2-carboxamide (1.61 g, 0.0078 mol); m.p. 258°-260° C. (dec.); [α]= −73.8° (c=1.4%, MeOH).

Alternatively Compound (Q) may be prepared starting from the mother liquors of salt precipitation, first and second crystallisation of alternative Preparation (O)(i') by the following method : the methanol solution is evaporated off to dryness and the residue is taken up in 1N HCl. The obtained solution is washed with ethyl acetate, made basic by the addition of 1N NaOH and extracted with ethyl acetate. The organic extract is concentrated to dryness, the residue is dissolved in methanol and the equimolar amount of D(−)-mandelic acid is then added thereto. The precipitate is recovered by filtration and crystallised from MeOH seven times affording a product with [α]= −90.5° (c=1.4%, MeOH). The thus obtained salt is then dissolved in 0.1N HCl and the solution is washed with ethyl acetate, made basic by the addition of aqueous sodium carbonate, and extracted with ethyl acetate. The organic phase is dried, filtered and evaporated to dryness. The residue is dissolved in isopropanol and HCl saturated isopropanol is added thereto Compound (Q) is recovered by filtration. [α]= −76.4° (c=1.4%, MeOH)

Preparation (R)

(−) 2-aminomethyl-6-hydroxy-1,2,3,4-tetrahydronaphthalene hydrobromide [(2S) or (2R)-aminomethyl-6-hydroxy-1,2,3,4-tetrahydronaphthalene hydrobromide]

The above compound is obtained by following the procedure described in Preparation (P) but starting from the compound of Preparation (Q) (0.75 g, 0.0033 mol). M.p. 250°-252° C.; [α]= −64.2° (c=1.4%, MeOH).

Preparation (S)

Ethyl [(2(R)-aminomethyl-1,2,3,4-tetrahydronalphth-7-yl)oxy]acetate hydrochloride (i) 2(R)-(N-tertbutoxycarbonyl)aminomethyl-1,2,3,4-tetra hydronaphthalene A suspension of the Compound obtained in Preparation (H) as the free base (4.6 g, 0.026 mol) in dimethylformamide (60 ml) and triethylamine (3.6 ml, 0.026 mol) is stirred for 15 minutes at room temperature and then 90 % di-tertbutyl-di-carbonate (6.3 g, 0.026 mol) is added thereto. After stirring for 3 hours at room temperature, the reaction mixture is poured into water (about 300 ml) and extracted with ethyl acetate. The organic phase is washed with water, dried and evaporated to dryness. The residue is purified by flash chromatography eluting with ethyl acetate/cyclohexane 2/8.

(ii) Ethyl [(2(R)-(N-tertbutoxycarbonyl)aminomethyl-1,2,3,4-tetrahydronaphth-7-yl)oxy]acetate A mixture of the above product (3.6 g, 0.013 mol), and powdered potassium carbonate (4,4 g, 0.03 mol) in acetone (100 ml) is stirred at room temperature for 1 hour and then ethyl bromoacetate (5.1 g, 0.03 mol) is added thereto. The reaction mixture is refluxed for 5 hours, filtered and concentrated under reduced pressure. The residue is dissolved in ethyl ether, the organic solution is washed with water, dried and evaporated to dryness under reduced pressure. The obtained residue is washed with a small amount of isopropyl ether affording ethyl [(2R) 2-(N-tertbutoxycarbonyl)aminomethyl-1,2,3,4-tetrahydronaphth-7-yl) oxy]acetate (2.3 g).

(iii) Ethyl [((2R) 2-aminomethyl-1,2,3,4-tetrahydronaphth-7-yl)oxy]acetate hydrochloride A 7.2N solution of hydrogen chloride in ethanol (5 ml) is added to a solution of the compound obtained in step (ii) above (2.3 g, 0.0063 mol) in absolute ethanol (15 ml) and the obtained mixture is heated to 50° C. for 30 minutes, and then concentrated under reduced pressure. The residue is washed with a small amount of acetone affording the compound indicated in the title (1.4 g).

Preparation (T)

Ethyl [(2(S)-aminomethyl-1,2,3,4-tetrahydronaphth-7-Yl)oxy-]acetate hydrochloride (i) 2(S)-(N-tertbutoxycarbonyl)aminomethyl-1,2,3,4-tetra hydronaphthalene The above product (2.2 g) is obtained by following the procedure described in Preparation (S)(i) but starting from the Compound of Preparation (I) (2.1 g, 0.012 mol).

(ii) Ethyl [(2(S)-(N-tertbutoxycarbonyl)aminomethyl-1,2,3,4-tetrahydronaphth-7-yl)oxy]acetate The above compound (1.4 g) is obtained by following the procedure described in Preaparation (S)(ii) but starting from the compound obtained in step (i) above (2.2 g, 0.008 mol).

(iii) Ethyl [((2S) 2-aminomethyl-1,2,3,4-tetrahydronaphth-7-yl)oxy]acetate hydrochloride The compound indicated in the title (0.8 g) is obtained starting from the product of step (ii) above and following the procedure of Preparation (S)(iii).

Preparation (U)

Ethyl [((2S) 2-aminomethyl-1,2,3,4-tetrahydronaphth-6yl)-oxy]acetate hydrochloride and Preparation (V)

Ethyl [((2R) 2-aminomethyl-1,2,3,4-tetrahydronaphth-6-yl)-oxy]acetate hydrochloride The compounds indicated above are obtained in yields of from 15 to 20%, by following the procedure described in Preparation (S), steps (i), (ii), and (iii), but starting from the compounds of Preparation (P) and (R).

In the case of the 6-substituted derivatives, assignement of the (R) absolute configuration to the dextrorotatory enantiomer and of the (S) absolute configuration to the levorotatory isomer, even if likely, has not been confirmed.

As a matter of fact, unlike the 7-substituted derivatives, where absolute configuration has been easily attributed to the starting parent compound (see Preparation (F)(i)) by comparison with known compounds, within the series of 6-substituted derivatives, this method cannot be employed as the optically active compounds which, by analogy, should be used as reference compounds, are not described in the literature.

EXAMPLE 1

N-[(2(R)-7-hydroxy-1,2,3,4-tetrahydronaphth-2-yl)methyl]-(2R)-2-hydroxy-2-(3-chlorophenyl)ethanamine hydrochloride (i) N-[(2(R)-7-hydroxy-1,2,3,4-tetrahydronaphth-2-yl)methyl]-(R)-3-chloromandelamide A suspension of the product of Preparation (H) above (2.2 g, 0.013 mol), (R)-3-chloromandelic acid (2.3 g, 0.013 mol), benzotriazolyl-N-oxytris-(dimethylamino)-phosphonium hexafluorophosphate (BOP)(5.2 g, 0.013 mol) in anhydrous methylene chloride (100 ml) and triethylamine (1.8 ml, 1.3 g, 0.013 mol) is stirred at room temperature for 5 hours. Saline (50 ml) is then added thereto and the mixture is stirred for further 30 minutes. The organic phase is separated, washed sequentially with 2N HCl (2×30 ml), water, saturated sodium bicarbonate, and water. Then it is dried and evaporated to dryness. The obtained product is purified by flash chromatography eluting with a mixture ethyl acetate/cyclohexane 1/1. The thus obtained oily product is dried under reduced pressure at 40° C. for 2 days yielding the above indicated amide as a vitreous powder; $[\alpha] = +31.6°$ (c=1%, MeOH).

(ii) N-[(2(R)-7-hydroxy-1,2,3,4-tetrahydronaphth-2-yl)methyl]-(2R)-2-hydroxy-2-(3-chlorophenyl)ethanamine hydrochloride A solution of the compound obtained in step (i) above (2.7 g, 0.008 mol) in anhydrous tetrahydrofuran (50 ml) is heated to the reflux temperature under nitrogen atmosphere and a 10M solution of borane-methyl sulfide (2.4 ml, 0.024 mol) in anhydrous tetrahydrofuran (20 ml) is slowly dripped in. The thus obtained reaction mixture is refluxed for 4 hours, then it is cooled and methanol (20 ml) is added thereto dropwise. The mixture is refluxed for 30 minutes and concentrated to dryness and the product, obtained as the free base, is purified by flash chromatography eluting with methanol. The obtained base is dissolved in acetone (40 ml) and the solution is made acidic by the addition of hydrochloric acid saturated isopropanol, thus affording the compound indicated in the title (1 g) which is then dried under reduced pressure, at 40° C.; for 2 days. M.p. 145°–148° C.; $[\alpha] = +34°$ (c=1%, MeOH).

EXAMPLE 2

N-[(2(S)-7-hydroxy-1,2,3,4-tetrahydronaphth-2-yl)methyl]-(2R)-2-hydroxy-2-(3-chlorophenyl)ethanamine (i) N-[(2(S)-7-hydroxy-1,2,3,4-tetrahydronaphth-2-yl)methyl]-(R)-3-chloromandelamide The above amide (4 g) is obtained as a vitreous powder, by following the procedure of Example 1 step (i) but starting from a mixture of the product of Preparation (I) (3.0 g, 0.017 mol), (R)-3-chloromandelic acid 3.2 g, 0.017 mol), BOP (6.8 g, 0.017 mol) and triethylamine (2.4 ml, 0.017 mol) in anhydrous methylene chloride (120 ml); [α]= −80.6° (c=1%, MeOH).

(ii) N-[(2(S)-7-hydroxy-1,2,3,4-tetrahydronaphth-2-yl)methyl]-(2R)-2-hydroxy-2-(3-chlorophenyl)ethanamine By following the procedure of Example 1 step (ii), but starting from the above amide (3.6 g, 0.010 mol), the desired product is obtained as the free base. The obtained compound is then purified by flash chromatography eluting with a mixture methanol/ethyl acetate 60/40 and then by crystallisation from methanol. Yield 1.9 g. M.p. 159°-161 ° C.; [α]= −77.2° (c=0.5%, MeOH).

EXAMPLE 3

N-[(8-hydroxy-1,2,3,4-tetrahydronaphth-2-yl)methyl]-2-hydroxy-2-(3-chloroohenyl)ethanamine hydrochloride (i) N-[(8-hydroxy-1,2,3,4-tetrahydronaphth-2-yl)methyl]-3-chloromandelamide A mixture of the compound obtained in Preparation (D) (2.2 g, 0.0085 mol), 3-chloromandelic acid (1.6 g, 0.0085 mol), BOP (3.4 g, 0.0085 mol), and triethylamine (2.4 ml, 1.72 g, 0.017 mol) in methylene chloride (50 ml) is stirred at room temperature for 5 hours. The mixture is then diluted with ethyl acetate, washed sequentially with water, diluted hydrochloric acid, saturated aqueous sodium bicarbonate, and water, dried and evaporated to dryness. The above amide (1.6 g) is then obtained with an IR absorption spectrum that corresponds to the assigned structure. IR (KBr) : 3342 (d) : O-H, CON-H; 1641 : HNC=O cm$^{-1}$.

(ii) N-[(8-hydroxy-1,2,3.4-tetrahydronaphth-2-yl)methyl]-2-hydroxy-2-(3-chlorophenyl)ethanamine hydrochloride A solution of the product of step (i) above (1.6 g, 0.0046 mol) in anhydrous tetrahydrofuran (30 ml) is heated to the reflux temperature under nitrogen atmosphere and a mixture of a 10M solution of boranemethyl sulfide (1.4 ml, 0.0014 mol) and anhydrous tetrahydrofuran (10 ml) is slowly dripped in. The obtained solution is refluxed for 4 hours and then diluted with methanol (10 ml). The solvent is evaporated off under vacuum and the obtained residue is dissolved in ethyl ether. The organic solution is made acidic by the addition of HCl saturated isopropanol and the product of the title is obtained therefrom by filtration (0.9 g) M.p. 175°-178° C.

EXAMPLES 4 to 9

By using the general procedure described in the foregoing Examples 1 to 3, but starting from 3-chloromandelic acid and the suitably selected 1,2,3,4-tetrahydronaphthalene derivatives, the following compounds of formula (I) are obtained via the intermediate compounds of formula (IV) indicated between parentheses and characterised by the reported IR absorption maxima.

EXAMPLE 4

N-[(7-methoxy-1,2,3,4-tetrahydronaphth-2-yl)methyl]-2-hydroxy-2-(3-chlorophenyl)ethanamine hydrochloride M.p. 170°-173° C. (isopropanol].
[N-[(7-methoxy-1,2,3,4-tetrahydronaphth-2-yl)methyl]-3-chloromandelamide]

IR (neat): 3390 (sh), 3324: O—H, CON—H; 1655: NHC=O cm$^{-1}$.

EXAMPLE 5

N-[(6-methoxy-1,2,3,4-tetrahydronaphth-2-yl)methyl]-2-hydroxy-2-(3-chlorophenyl)ethanamine hydrochloride M.p. 205°-208° C. (absolute ethanol).
[N-[(6-methoxy-1,2,3,4-tetrahydronaphth-2-yl)methyl]-3-chloromandelamide].

IR (KBr): 3520 (sh), 3300 (sh), 3247: O—H, CON—H; 1627, 1650: NHC=O cm$^{-1}$.

EXAMPLE 6

N-[(6-hydroxy-1,2,3,4-tetrahydronaphth-2-yl)methyl]-2-hydroxy-2-(3-chlorophenyl)ethanamine hydrochloride M.p. 174°-176° C. (isopropanol).
[N-[(6-hydroxy-1,2,3.4-tetrahydronaphth-2-yl-)methyl]-3-chloromandelamide].

IR (KBr): 3349 (b): O—H, CON—H; 1659: NHC=O cm$^{-1}$.

EXAMPLE 7

N-[(5-hydroxy-1,2,3,4-tetrahydronaphth-2-yl)methyl]-2-hydroxy-2-(3-chlorophenyl)ethanamine hydrochloride M.p. 177°-180° C. (triturated in acetone).
[N-[(5-hydroxy-1,2,3,4-tetrahydronaphth-2-yl)methyl]-3-chloromandelamide].

IR (KBr): 3365 (b): O—H, CON—H; 1659: NHC=O cm$^{-1}$.

EXAMPLE 8

N-[(8-methoxy-1,2,3,4-tetrahydronaphth-2-yl)methyl]-2-hydroxy-2-(3-chlorophenyl)ethanamine hydrochloride M.p. 186°-188° C. (isopropanol).
[N-[(8-methoxy-1,2,3,4-tetrahydronaphth-2-yl)methyl]-3-chloromandelamide].

IR (KBr): 3319 (d): O—H, CON—H; 1658: NHC=O cm$^{-1}$.

EXAMPLE 9

N-[(5-methoxy-1,2,3,4-tetrahydronaphth-2-yl)methyl]-2-hydroxy-2-(3-chlorophenyl)ethanamine hydrochloride M.p. 216°-218° C. (95% ethanol).
[N-[(5-methoxy-1,2,3,4-tetrahydronaphth-2-yl)methyl]-3-chloromandelamide; m.p. 92°-95° C.].

EXAMPLE 10

N-[(7-hydroxy-1,2,3,4-tetrahydronaphth-2-yl)methyl]-2-hydroxy-2-(3-chlorophenyl)ethanamine oxalate This compound is prepared by following the procedure described in Example 1 steps (i) and (ii), but starting from the compound of Preparation (M) and treating the product obtained as the free base with a solution of oxalic acid in acetone. M.p. 218°-220° C. (triturated in acetone).

EXAMPLE 11

Ethyl
[[2-[N-[2-(3-chlorophenyl)-2-hydroxy]ethyl-]aminomethyl-1,2,3,4-tetrahydronaphth-7-yl]oxy]acetate hydrochloride A mixture of the product of Preparation (K), as the free base (2.8 g, 0.010 mol) and 3-chlorostyrene oxide (2.6 g, 0.015 mol) in anhydrous dimethyl sulfoxide (15 ml) is heated to 80° C. for 8 hours under stirring The reaction mixture is poured into water and the solution is extracted with ethyl acetate. The organic phase is separated, washed with water, dried over sodium sulfate, filtered and evaporated to dryness. The residue is dissolved in hot isopropanol (40 ml) and HCl saturated isopropanol is then added thereto. The compound indicated in the title is recovered by filtration affording 1.4 g of a product with m.p. 157°–161° C.

EXAMPLE 12

Ethyl
4[[2-[N-[2-(3-chlorophenyl)-2-hydroxy]ethyl-]aminomethyl-1,2,3,4-tetrahydronaphth-7-yl]oxy]-butanoate hydrochloride The compound indicated in the title is obtained by using the same procedure as in Example 11 but starting from the compound of Preparation (L). M.p. 138°–145° C. (isopropanol).

EXAMPLE 13

N-[(7-methoxy-1,2,3,4-tetrahydronaphth-2-yl)methyl]-2-hydroxy-2-(3,4-dichlorophenyl)ethanamine hydrochloride (i) N-[(7-methoxy-1,2,3,4-tetrahydronaphth-2-yl)methyl]3,4-dichloromandelamide By following the procedure of Example 1(i) but starting from 3,4-dichloromandelic acid (3.1 g, 0.014 mol) and 2-aminomethyl-7-methoxy-1,2,3,4-tetrahydronaphthalene (2.67 g, 0.014 mol), N-[(7-methoxy-1,2,3,4-tetrahydronaphth-2-yl) methyl]-3,4-dichloromandelamide (4.5 g) is obtained as an oily product characterised by the following IR absorption maxima 3380 (b): O—H, CON—H; and 1641: NHC=O cm$^{-1}$.

(ii) N-[(7-methoxy-1,2,3,4-tetrahydronaphth-2-yl)methyl]-2-hydroxy-2-(3,4-dichlorophenyl)ethanamine hydrochloride.

A solution of the product obtained in above step (i) (4.5 g, 0.0114 mol) in tetrahydrofuran (75 ml) is heated to the reflux temperature under nitrogen atmosphere and a mixture of a 10M solution of borane-methyl sulfide (3.5 ml, 0.035 mol) and tetrahydrofuran (10 ml) is slowly added thereto. The resulting solution is refluxed for 4 hours then methanol (25 ml) is slowly dripped in The solution is concentrated under reduced pressure, the residue is dissolved in isopropanol and precipitated therefrom by the addition of HCl in isopropanol. The obtained product is crystallised from ethanol affording 1.87 g of the compound of the title. M.p. 194°–198° C.

EXAMPLE 14

Ethyl
[[2-[N-(2-phenyl)-2-hydroxy]ethyl]aminomethyl-1,2,3,4-tetrahydronaphth-7-yl]oxy]acetate hydrochloride The compound of the title is obtained by using the procedure of Example 11 but replacing 3-chlorostyrene oxide with styrene oxide. M.p. 163°–170° C. (isopropanol).

EXAMPLE 15

N-[(7-methoxy-1,2,3,4-tetrahydronaphth-2-yl)methyl]-2-hydroxy-2-phenylethanamine hydrochloride A mixture of styrene oxide (1 g, 0.0083 mol), 2-aminomethyl -7-methoxy-1,2,3,4-tetrahydronalphthalene (1.5 g, 0.0078 mol) in dimethylsulfoxide (20 ml) is heated to 80° C. ext. for 10 hours. The reaction mixture is then poured into water and the solution is extracted with ethyl acetate. The organic phase is separated, washed with water, dried and evaporated to dryness The obtained oily residue is purified by flash chromatography eluting with a mixture methylene chloride/methanol 95/5. The combined fractions are evaporated off, the obtained residue is dissolved in ethyl ether and HCl saturated isopropanol is then added thereto. The precipitate is filtered yielding 0.5 g of the compound of the title. M.p. 187°–192° C.

EXAMPLE 16

N-[(7-hydroxy-1,2,3,4-tetrahydronaphth-2-yl)methyl]-2-hydroxy-2-phenylethanamine hydrochloride By following the procedure of Example 15 but replacing 2-aminomethyl-7-methoxy-1,2,3,4-tetrahydronalohthalene with the compound of Preparation (M) a product is obtained which is washed with a small amount of acetone thus affording the compound of the title with m.p. 155°–158° C.

EXAMPLE 17

N-[(1,2,3,4-tetrahydronaphth-2-yl)-methyl]-2-hydroxy-2-(3-chloro)ohenylethanamine hydrochloride A mixture of 2-amino-1,2,3,4-tetrahydronaphthalene free base (1.4 g, 0.0087 mol) obtained by neutralisation of the corresponding hydrochloride (Preparation (N)) with sodium hydroxide and extraction with ethyl acetate, and 3-chlorostyrene oxide (2 g, 0.013 mol) in dimethylsulfoxide (15 ml) is heated to 80° C. ext. for 8 hours. The reaction mixture is then poured into water (about 100 ml) and the solution is extracted with ethyl ether. The organic phase is washed with water, dried and evaporated to dryness. The residue is taken up in petroleum ether and filtered. The obtained product (1.5 g) is dissolved in acetone (50 ml) under gentle heating and HCl saturated isopropanol is added thereto. The precipitate which forms is recovered by filtration affording 1.5 g of the compound of the title; m.p. 232°–235° C.

EXAMPLE 18

[[2-[N-(2-(3-chlorophenyl)-2-hydroxy]ethyl-]aminomethyl-1,2,3,4-tetrahydronaphth-7-yl]oxy]acetic acid A mixture of the compound of Example 11, as free base, (2.0 g, 0.0047 mol) and potassium hydroxide (0.3 g, 0.0057 mol), in 95% ethanol (30 ml) and water (30 ml) is heated to 50° C. for 5 hours, then ethanol is evaporated off and water (20 ml) is added. The aqueous solution is extracted with ethyl ether (2×50 ml). The organic phase is treated with carbon, and filtered and 1N HCl is then added thereto up to pH 6.5. The precipitate which forms is recovered by filtration affording the compound of the title with m.p. 213°–217° C.

EXAMPLE 19

N-[((2R) or (2S)
6-hydroxy-1,2,3,4-tetrahydronaphth-2-yl)
methyl]-(2R)-2-hydroxy-2-(3-chlorophenyl)ethanamine
hydrochloride (i) N-[(2R) or (2S) 6-hydroxy-1,2,3,4-tetrahydronaphth-2-yl)methyl]-(R)-3-chloromandelamide A mixture of the compound of Preparation (P) (0.6 g, 0.0023 mol), (R)-3-chloromandelic acid (0.4 g, 0.0023 mol), BOP (1 g, 0.0023 mol) and triethylamine (1.8 ml, 1.3 g, 0.013 mol) in methylene chloride (20 ml), is stirred at room temperature overnight. Ethyl acetate (60 ml) is then added thereto and the mixture is washed sequentially with 2N HCl, a saturated sodium bicarbonate solution, and water. The organic phase is separated, dried and concentrated to dryness. The residue is purified by chromatography eluting with a mixture ethyl acetate/cyclohexane 1/1, thus affording 0.7 g of the above indicated amide. [α]= +21.9° (c=1%, MeOH).

(ii) N-[((2R) or (2S) 6-hydroxy-1,2,3,4-tetrahydronaphth-2-yl)methyl]-(2R)-2-hydroxy-2-(3-chlorophenyl)ethanamine hydrochloride A 10M solution of borane-methyl sulfide (0.5 ml, 0.005 mol) in anhydrous tetrahydrofuran (5 ml) is slowly added to a solution of the compound obtained in above step (i) (0.5 g, 0.0014 mol) in anhydrous tetrahydrofuran (20 ml) heated to the reflux temperature under nitrogen atmosphere. The thus obtained reaction mixture is refluxed for 4 hours, then methanol (5 ml) is slowly dripped in and 30 minutes later 1N HCl (4 ml) is added thereto. The mixture is refluxed for 30 minutes, concentrated under vacuum, made basic by the addition of ammonium hydroxide, and extracted with ethyl acetate. The organic phase is washed with water, dried and evaporated to dryness. The obtained residue is dissolved in hot isopropanol (10 ml), the solution is made acidic by the addition of HCl saturated isopropanol, and the precipitate which forms is recovered by filtration (0.24 g). M.p. 175°–177° C.; [α]= +18.3° (c=.1%, MeOH).

EXAMPLE 20

N-[((2S) or (2R)
6-hydroxy-1,2,3,4-tetrahydronaphth-2-yl)
methyl]-(2R)-2-hydroxy-2-(3-chlorophenyl)ethanamine
hydrochloride (i) N-[(2S) or (2R) 6-hydroxy-1,2,3,4-tetrahydronaphth-2-yl)methyl]-(R)-3-chloromandelamide The above amide (0.6 g) is obtained by following the procedure of Example 19 (i) but starting from the compound of Preparation (R) (0.5 g, 0.002 mol), (R)-3-chlormandelic acid (0.4 g, 0.002 mol), BOP (0.88 g, 0.002 mol) and triethylamine (0.6 ml, 0.4 g, 0.004 mol) in methylene chloride (20 ml). [α]= −75.1° (c=1%, MeOH).

(ii) N-[((2S) or (2R) 6-hydroxy-1,2,3,4-tetrahydronaphth-2-yl)methyl]-(2R)-2-hydroxy-2-(3-chlorophenyl)ethanamine hydrochloride The compound indicated in the title (0.34 g) is obtained by following the procedure described in Example 19 (ii) but starting from the amide obtained in step (i) above (0.5 g, 0.0014 mol). M.p. 217°–219° C. [α]= −72.2° (c=1%, MeOH).

EXAMPLE 21

N-[(6-hydroxy-1,2,3,4-tetrahydronaphth-2-yl)methyl]-
2-hydroxy-2-(4-chlorophenyl)ethanamine (i) N-[(6-hydroxy-1,2,3,4-tetrahydronaphth-2-yl)methyl]-4-chloromandelamide A mixture of the hydrobromide of the compound obtained in Preparation (J) (3.77 g, 0.015 mol), 4-chloromandelic acid (2.8 g, 0.015 mol), BOP (6.3 g, 0.015 mol) and triethylamine (3 g, 0.03 mol) in methylene chloride (80 ml) is stirred at room temperature overnight. Ethyl acetate is then added thereto, and the mixture is washed sequentially with water, 2N HCl, a saturated sodium bicarbonate solution and water. The solution is dried and concentrated under reduced pressure affording an oily product which is purified by chromatography eluting with a mixture ethyl acetate/cyclohexane 1/1 thus yielding 3.47 g of the above indicated amide.

(ii) N-[(6-hydroxy-1,2,3,4-tetrahydronaphth-2-yl)methyl]-2-hydroxy-2-(4-chlorophenyl)ethanamine A solution of the compound obtained in step (i) above (3.2 g, 0.0092 mol) in anhydrous tetrahydrofuran (65 ml) is heated to the reflux temperature under nitrogen atmosphere and a 10M solution of borane-methyl sulfide (2.8 ml, 0.028 mol) and anhydrous tetrahydrofuran (10 ml) are then added thereto. The mixture is refluxed for 4 hours, methanol (30 ml) is slowly added thereto and refluxing is prolonged for an additional hour. 1N HCl (60 ml) is then added thereto and the mixture is refluxed for 1 hour, and concentrated under reduced pressure. The residue is taken up in ethyl acetate, the organic solution is washed with ammonium hydroxide and then with water, dried over sodium sulfate, filtered and concentrated to dryness under reduced pressure affording a solid which is washed with isopropyl ether (2.3 g). M.p. 150°–153° C.

EXAMPLE 22

N-[(7-hydroxy-1,2,3,4-tetrahydronaphth-2-yl)methyl]-
2-hydroxy-2-(2-chlorophenyl)ethanamine fumarate (i) N-[(7-hydroxy-1,2,3,4-tetrahydronaphth-2-yl)methyl]-2-chloromandelamide The above amide (2.2 g) is prepared by following the procedure of Example 19 (i) but starting from the compound of Preparation (M) (1.5 g, 0.0085 mol), 2-chloromandelic acid (1.6 g, 0.0055 mol), BOP (3.75 g, 0.0085 mol) and triethylamine (0.86 g, 0.0085 mol) in methylene chloride (55 ml).

(ii) N-[(7-hydroxy-1,2,3,4-tetrahydronaphth-2-yl)methyl]-2-hydroxy-2-(2-chlorophenyl)ethanamine fumarate The compound of the title (0.09 g) is prepared by following the procedure of Example 19 (ii) but starting from the compound obtained in step (i) above (1.9 g, 0.0055 mol) and using fumaric acid in isopropanol instead of HCl saturated isopropanol. M.p. 215°–217° C.

EXAMPLE 23

N-[(7-hydroxy-1,2,3,4-tetrahydronaphth-2-yl)methyl]-
2-hydroxy-2-(4-chlorophenyl)ethanamine
hemifumarate (i) N-(7-hydroxy-1,2,3,4-tetrahyironaphth-2-yl)methyl]-4-chloromandelamide The above amide (2.2 g) is prepared by following the procedure of Example 19 (i) but starting from the compound of Preparation (M) (2 g, 0.0113 mol), 4-chloromandelic acid (2.1 g, 0.0113 mol), BOP (5 g, 0.0113 mol) and triethylamine (1.6 ml, 0.0113 mol) in methylene chloride (ii) N-[(7-hydroxy-1,2,3,4-tetrahydronaphth-2-yl)methyl]-2-hydroxy-2-(4-chlorophenyl)ethanamine hemifumarate The compound of the title (0.18 g) is prepared by following the procedure of Example 19 (ii) but starting from the amide obtained in step (i) above (2 g, 0.0058 mol) and using fumaric acid in isopropanol instead of HCl saturated isopropanol. M.p. 210°–213° C.

EXAMPLE 24

N-[(7-hydroxy-1,2,3,4-tetrahydronaphth-2-yl)methyl]-2-hydroxy-2-(3-methoxyphenyl)ethanamine hydrochloride (i) 3-methoxystyrene oxide A mixture of 3-methoxybenzaldehyde (13.4 g, 0.098 mol), a solution of sodium hydroxide (200 g) in water (200 ml), dodecyl-dimethylsulfonium methyl sulfate (51 g, 0.15 mol) and toluene (150 ml) is stirred for 17 hours. Ice is then added and the organic phase is separated, washed with water (3×50 ml), dried over sodium sulfate, filtered and concentrated under reduced pressure. The above product is recovered from the thus obtained residue by distillation at 135°–140° C. and 30 mmHg.

(ii) N-[(7-hydroxy-1,2,3,4-tetrahydronaphth-2-yl)methyl]-2-hydroxy-2-(3-methoxyphenyl)ethanamine hydrochloride A mixture of the above product, which has a titre of 71.5%, as determined by chromatography, (1.2 g, 0.0059 mol) and of the compound of Preparation (M) (1.4 g, 0.0079 mol) in absolute ethanol (60 ml) is refluxed overnight, then it is concentrated under reduced pressure. The oily residue is purified by chromatography eluting with ethyl acetate. The obtained product is dissolved in ethyl ether and HCl saturated isopropanol is then added thereto to precipitate the compound of the title (0.36 g).

EXAMPLE 25

N-[(6-hydroxy-1,2,3,4-tetrahydronaphth-2-yl)methyl]-2-hydroxy-2-(3-methoxyphenyl)ethanamine hydrochloride The compound of the title (0.62 g) is obtained by following the procedure of Example 24 (ii) but starting from the compound of Preparation (J) (1.9 g) instead of the compound of Preparation (M).

EXAMPLE 26

N-[(2(R) 7-methoxy-1,2,3,4-tetrahydronaphth-2-yl)methyl]-(2R)-2-hydroxy-2-(3-chlorophenyl)ethanamine hydrochloride A mixture of 2(R)-aminomethyl-7-methoxy-1,2,3,4-tetrahydronaphthalene hydrochloride (0.11 g, 0.48 mmol) (Preparation (G)), (R)-3-chlorostyrene oxide (0.07 g, 0.46 mmol), and triethylamine (0.13 ml, 0.96 mmol) in dimethylsulfoxide (5 ml) is heated to 60° C. ext. for 48 hours. The reaction mixture is then poured into water and the aqueous solution is extracted with ethyl acetate. The organic extract is washed with water, dried over sodium sulfate, filtered and concentrated to dryness.

The obtained residue is purified by flash chromatography eluting with methylene chloride.

The obtained product is dissolved in acetone and the compound of the title (0.02 g) is then precipitated therefrom by the addition of HCl saturated isopropanol and recovered by filtration. M.p. 214-216° C. $[\alpha] = +25.1°$ (c=1%, MeOH).

EXAMPLE 27

N-[(2(S) 7-methoxy-1,2,3,4-tetrahydronaphth-2-yl)methyl]-(2R)-2-hydroxy-2-(3-chlorophenyl)ethanamine hydrochloride The compound of the title (0.02 g) is prepared by following the same procedure as in Example 26 but starting from 2(S)-aminomethyl-7-methoxy-1,2,3,4-tetrahydronaphthalene hydrochloride (0.11 g, 0.48 mmol), (R)-3-chlorostyrene oxide (0.07 g, 0.46 mmol) and triethylamine (0.13 ml, 0.96 mmol) in dimethylsulfoxide (5 ml). M.p. 189°–191° C.; $[\alpha] = -70.7°$ (c =1%, MeOH).

EXAMPLE 28

N-[(2R) or (2S) 6-methoxy-1,2,3,4-tetrahydronaphth-2-yl) methyl]-(2R)-2-hydroxy-2-(3-chlorophenyl)ethanamine hydrochloride The compound of the title (0.5 g) is prepared by following the same procedure as in Example 26 but starting from (2R) (or (2S)) 2-aminomethyl-6-methoxy-1,2,3,4-tetrahydronaph-thalene (0.63 g, 0.0033 mol) obtained by neutralisation of the corresponding hydrochloride described in Preparation (O), and (R)-3-chlorostyrene oxide (0.6 g, 0.0039 mol) in dimethylsulfoxide (10 ml).

EXAMPLE 29

N-[((2S) or (2R) 6-methoxy-1,2,3,4-tetrahydronaphth-2-yl)-methyl]-(2R)-2-hydroxy-2-(3-chlorophenyl)ethanamine hydrochloride The compound of the title (0.4 g) is prepared by following the same procedure as in Example 26 but starting from (2S) (or (2R)) 2-aminomethyl-6-methoxy-1,2,3,4-tetrahydronaphth alene (0.5 g, 0.0026 mol) obtained by neutralisation of the corresponding hydrochloride described in Preparation (Q), and (R)-3-chlorostyrene oxide (0.6 g, 0.0039 mol) in dimethylsulfoxide (10 ml).

EXAMPLE 30

Ethyl [[2(R)-[N-(2-(3-chlorophenyl)-2(R)-hydroxy]ethyl]aminomethyl-1,2,3,4-tetrahydronaphth-7-yl]oxy]acetate hydrochloride A mixture of ethyl [[2(R)-aminomethyl-1,2,3,4-tetrahydronaphth-7-yl]oxy]acetate (1 g, 0.0038 mol) obtained by neutralisation of the corresponding hydrochloride described in Preparation (S), and (R)-3-chlorostyrene oxide (0.8 g, 0.0052 mol) in anhydrous dimethylsulfoxide (15 ml) is heated to 80° C. ext. under stirring for 10 hours, then it is poured into water and the solution is extracted with ethyl acetate. The organic extract is washed with water, dried over sodium sulfate, filtered and evaporated to dryness. The residue is dissolved in hot isopropanol and the compound of the title is then precipitated from the obtained solution by the addition of HCl saturated isopropanol (0.6 g).

EXAMPLE 31

Ethyl [[2(S)-[N-(2-(3-chlorophenyl)-2(R)-hydroxy]ethyl]aminomethyl-1,2,3,4-tetrahydronaphth-7-yl]oxy]acetate hydrochloride The compound indicated in the title (0.5 g) is obtained by using the same procedure as in Example 30 but starting from ethyl [[2(S)-aminomethyl-1,2,3,4-tetrahydronaphth-7-yl]oxy]acetate (1 g, 0.0038 mol) obtained by neutralisation of the corresponding hydrochloride described in Preparation (T), instead of the (R) enantiomer.

EXAMPLE 32

Ethyl [[2(R) (or 2(S))-[N-(2-(3-chlorophenyl)-2(R)-hydroxy]ethyl]aminomethyl-1,2,3,4-tetrahydronaphth-6-yl]oxy]acetate hydrochloride The compound indicated in the title (1.2 g) is obtained by using the same procedure as in Example 30 but starting from a mixture of ethyl [[2(R) (or 2(S))-aminomethyl-1,2,3,4-tetrahydronaphth-6-yl]oxy]acetate (2.2 g, 0.0083 mol) obtained by neutralisation of the corresponding hydrochloride described in Preparation (U), and (R)-3-chlorostyrene oxide (1.8 g, 0.012 mol) in anhydrous dimethylsulfoxide (20 ml).

EXAMPLE 33

Ethyl [[2(S) (or 2(R)) TM [N-(2-(3-chlorophenyl)-2(R)-hydroxy]ethyl]aminomethyl-1,2,3,4-tetrahyironaphth-6-yl-]oxy]acetate hydrochloride The compound indicated in the title (1.1 g) is obtained by using the same procedure as in Example 30 but starting from a mxture of ethyl [[2(S) (or 2(R))-aminomethyl-1,2,3,4-tetranydronaphth-6-yl]oxy]acetate (1.8 g, 0.0068 mol) obtained by neutralisation of the corresponding hydrochloride described in Preparation (V), and (R)-3-chlorostyrene oxide (1.5 g, 0.0097 mol) in anhydrous dimethylsulfoxide (20 ml).

EXAMPLE 34

Tablets containing the compound of Example 6 as the active ingredient and having the following composition

| Compound of Example 6 | 20 mg |
| Microcristalline cellulose | 30 mg |
| Dried corn starch | 30 mg |
| Lactose | 100 mg |
| Magnesium stearate | 5 mg | are prepared by grinding the active ingredient up to a particle size of 0.4 mm, sifting the obtained powder by a 0.4 mm sieve, mixing all the above ingredients together and compressing the obtained mixture in tablets.

Analogously, tablets containing 40 mg of active ingredient each can be prepared.

EXAMPLE 35

By operating as described in Example 34 but using the compound of Example 7 as the active ingredient, tablets of the following composition can be prepared:

| Compound of Example 7 | 50.0 mg |
| Dried corn starch | 100.0 mg |
| Lactose | 95.0 mg |
| Talc | 4.5 mg |
| Magnesium stearate | 0.5 mg |

EXAMPLE 36

10,000 capsules, each containing 50 mg of active principle are prepared starting from the following ingredients Compound of Example 4 (500 g), microcrystalline cellulose (495 g), amorphous silica gel (5 g). The above ingredients are admixed together and filled into hard gelatin capsules of size 4.

EXAMPLE 37

An aqueous sterile solution suitable for the preparation of vials for parenteral administration, containing the compound of Example 6 as the active ingredient is prepared with the following composition

| Compound of Example 6 | 30 mg |
| Sodium chloride | 5 mg |
| Distilled water | q.s. to 2 ml |

EXAMPLE 38

An ophthalmic solution is prepared by mixing the following ingredients according to conventional techniques

| Compound of Example 4 | 1.0 mg |
| $NaH_2PO_4$ | 10.4 mg |
| $Na_2HPO_4$ | 2.4 mg |
| Chlorobutanol | 5.0 mg |
| Hydroxypropylmethylcellulose | 5.0 mg |
| 1N NaOH | q.s. to pH = 7.4 |
| Distilled water | q.s. to 1.0 ml |

We claim:

1. A phenylethanolaminomethyltetraline of formula (I)

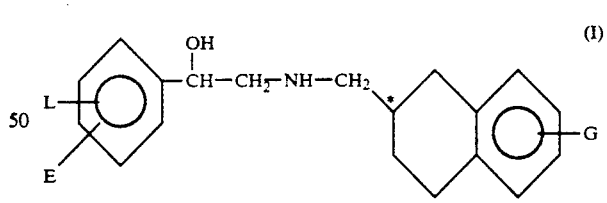

wherein
E represents hydrogen, $(C_1-C_4)$alkyl, $(C_1-C_4)$alkoxy, phenyl, nitro, halogen, or trifluoromethyl,
L represents hydrogen, $(C_1-C_4)$alkyl, $(C_1-C_4)$alkoxy, phenyl, nitro, or halogen, or
E and L taken together represent a group —CH═CH—CH═CH— or —CH$_2$—CH$_2$—CH$_2$—CH$_2$—, and
G represents hydrogen, chloro, hydroxy or an —OG' group wherein G' represents a $(C_1-C_4)$alkyl group either unsubstituted or substituted with hydroxy, $(C_1-C_4)$alkoxy, $(C_1-C_4)$alkoxycarbonyl, carboxy, or $(C_3-C_7)$cycloalkyl; a $(C_3-C_7)$cycloalkyl group; or a $(C_2-C_4)$alkanoyl group; and salts thereof.

2. A compound of claim 1 wherein G represents hydrogen, hydroxy or a group —OG' wherein G' represents unsubstituted or substituted ($C_1$-$C_4$)alkyl.

3. A compound of claim 2 wherein G represents hydrogen, hydroxy or a group —OG' wherein G' represents (Chd 1-$C_4$)alkyl unsubstituted or substituted with carbo($C_1$-$C_4$)alkoxy or carboxy.

4. A compound as in any of claims 1 to 3 wherein the chiral carbon atom in the ethanolamino chain has absolute configuration (R).

5. A pharmaceutical composition containing one or more compounds of claim 1 as the main active ingredient.

6. The pharmaceutical composition of claim 5 for systemic administration in unit dosage form containing from 0.1 to 500 mg of active principle.

7. The pharmaceutical composition of claim 5 containing from 10 ng to 1 mg of active principle per unit dosage form.

* * * * *

UNITED STATES PATENT AND TRADEMARK OFFICE
CERTIFICATE OF CORRECTION

PATENT NO. : 5,130,339

DATED : July 14, 1992

INVENTOR(S) : Roberto CECCHI et al.

It is certified that error appears in the above-identified patent and that said Letters Patent is hereby corrected as shown below:

ON THE COVER PAGE:

Item [21], delete "301,050" and insert --635,950--

Signed and Sealed this

Sixteenth Day of November, 1993

BRUCE LEHMAN

*Attest:*

*Attesting Officer*   Commissioner of Patents and Trademarks